United States Patent
Duffield et al.

(10) Patent No.: US 11,103,498 B2
(45) Date of Patent: Aug. 31, 2021

(54) PHARMACEUTICAL COMPOSITIONS

(71) Applicant: ADEPTIO PHARMACEUTICALS LIMITED, London (GB)

(72) Inventors: Andrew John Duffield, Berkhamsted (GB); Anant Pandya, Croydon (GB)

(73) Assignee: ADEPTIO PHARMACEUTICALS LIMITED, London (GB)

(*) Notice: Subject to any disclaimer, the term of this patent is extended or adjusted under 35 U.S.C. 154(b) by 0 days.

(21) Appl. No.: 16/852,008

(22) Filed: Apr. 17, 2020

(65) Prior Publication Data

US 2020/0246324 A1    Aug. 6, 2020

Related U.S. Application Data

(62) Division of application No. 15/939,826, filed on Mar. 29, 2018, now Pat. No. 10,660,885.

(30) Foreign Application Priority Data

Apr. 1, 2017 (GB) ..................................... 1705303

(51) Int. Cl.
| | | |
|---|---|---|
| *A61K 9/48* | (2006.01) | |
| *A61K 9/20* | (2006.01) | |
| *A61K 9/28* | (2006.01) | |
| *A61P 25/14* | (2006.01) | |
| *C07D 471/04* | (2006.01) | |
| *C07D 455/06* | (2006.01) | |
| *A61K 31/473* | (2006.01) | |

(52) U.S. Cl.
CPC .............. *A61K 31/473* (2013.01); *A61K 9/20* (2013.01); *A61K 9/2846* (2013.01); *A61P 25/14* (2018.01); *C07D 455/06* (2013.01); *C07D 471/04* (2013.01); *A61K 9/48* (2013.01)

(58) Field of Classification Search
CPC ... A61K 9/48; A61K 9/20; A61K 9/28; A61K 31/473; A61P 25/14; C07D 471/04; C07D 455/06

See application file for complete search history.

(56) References Cited

U.S. PATENT DOCUMENTS

| | | | |
|---|---|---|---|
| 7,919,622 | B2 | 4/2011 | Amarasinghe et al. |
| 8,039,627 | B2 | 10/2011 | Gano |
| 10,660,885 | B2 | 5/2020 | Duffield et al. |
| 2010/0087475 | A1 | 4/2010 | Duffield et al. |
| 2012/0003330 | A1 | 1/2012 | Gant et al. |
| 2018/0280359 | A1 | 10/2018 | Duffield et al. |
| 2018/0280360 | A1 | 10/2018 | Duffield et al. |
| 2018/0280361 | A1 | 10/2018 | Duffield et al. |
| 2018/0280374 | A1 | 10/2018 | Duffield et al. |
| 2019/0111035 | A1 | 4/2019 | Duffield et al. |

FOREIGN PATENT DOCUMENTS

| | | |
|---|---|---|
| CN | 102285984 A | 12/2011 |
| GB | 800969 A | 9/1958 |
| WO | 2005077946 A1 | 8/2005 |
| WO | 2006053067 A2 | 5/2006 |
| WO | 2007007105 A1 | 1/2007 |
| WO | 2007017654 A1 | 2/2007 |
| WO | 2008058261 A1 | 5/2008 |
| WO | 2009073677 A1 | 6/2009 |
| WO | 2010018408 A2 | 2/2010 |
| WO | 2010026436 A2 | 3/2010 |
| WO | 2011153157 A2 | 12/2011 |
| WO | 2014047167 A1 | 3/2014 |
| WO | 2015120110 A2 | 8/2015 |
| WO | 2015171802 A1 | 11/2015 |
| WO | 2016127133 A1 | 8/2016 |
| WO | 2016210180 A2 | 12/2016 |
| WO | 2017112857 A1 | 6/2017 |
| WO | 2018140092 A1 | 8/2018 |
| WO | 2018140093 A1 | 8/2018 |
| WO | 2018140094 A1 | 8/2018 |
| WO | 2018140095 A2 | 8/2018 |
| WO | 2018140096 A1 | 8/2018 |

OTHER PUBLICATIONS

Yao, et al., "Preparation and Evaluation of Tetrabenazine Enantiomers and All Eight Stereoisomers of Dihydrotetrabenazine as VMAT2 Inhibitors", Eur. J. Med. Chem., 46, pp. 1841-1848, (2011).

Kilbourn, et al., "Binding of α-dihydrotetrabenazine to the Vesicular Monoamine Transporter is Stereospecific", Eur. J. Pharmacol., 278(3), pp. 249-252, (1995).

Bhatnagar, et al., "Pharmacokinetics of Dihydrotetrabenazine After Intravenous and Peroral Administration to Rats", Pharm Pharmacol Lett, 2(3), pp. 89-91, (1992).

Mehvar, et al., "Pharmacokinetics of Tetrabenazine and its Major Metabolite in Man and Rat", Drug Metab. Dispos., 15(2), pp. 250-255, (1987).

Roberts, et al., "The Pharmacokinetics of Tetrabenazine and its Hydroxy Metabolite in Patients Treated for Involuntary Movement Disorders", Eur. J. Clin. Pharmacol., 29, pp. 703-708., (1986).

Kilbourn, et al., "Absolute Configuration of (+)-α-Dihydrotetrabenazine, an Active Metabolite of Tetrabenazine", Chirality, 9, pp. 59-62, (1997).

Brossi, et al., "Syntheseversuche in der Emetin-Reihe, 3. Mittelung", Helv. Chim Acta., vol. XLI, No. 193, pp. 1793-1806, (1958) (and English Translation).

Schwartz, et al, "Metabolic Studies of Tetrabenazine, A Psychotropic Drug in Animals and Man", Biochem. Pharmacol., 15, pp. 645-655, (1956).

(Continued)

*Primary Examiner* — Sun Jae Yoo
(74) *Attorney, Agent, or Firm* — Heslin Rothenberg Farley & Mesiti P.C.

(57) ABSTRACT

The invention provides (+)-α-dihydrotetrabenazine succinate salt.

Also provided are (+)-α-dihydrotetrabenazine succinate salt for use in medicine, pharmaceutical compositions comprising (+)-α-dihydrotetrabenazine succinate salt and a pharmaceutically acceptable excipient and the uses of (+)-α-dihydrotetrabenazine succinate salt as a VMAT2 receptor antagonist and in the treatment of a movement disorder such as Tourette's syndrome.

The invention further provides a method for preparing the (+)-α-dihydrotetrabenazine succinate salt.

16 Claims, 8 Drawing Sheets

(56) References Cited

OTHER PUBLICATIONS

Scherman, et al., "Hydrophobicity of the Tetrabenazine-Binding Site of the Chromaffin Granule Monoamine Transporter", Mol. Pharmacol., 33, pp. 72-77, (1987).
Mehvar, et al., "Concentration-Effect Relationships of Tetrabenazine and Dihydrotetrabenazine in the Rat", J. Pharm. Sci., 76(6), pp. 461-465, (1987).
Kilbourn, et al., "PET Radioligands for Vesicular Neurotransmitter Transporters", Med. Chem. Res., 5, pp. 113-126, (1994).
Kilbourn, et al., "In Vivo Measures of Dopaminergic Radioligands in the Rat Brain: Equilibrium Infusion Studies", Synapse, 43, pp. 188-194, (2002).
Müller, "Valbenazine Granted Breakthrough Drug Status for Treating Tardive Dyskinesia", Expert Opin. Investig. Drugs, 24(6), pp. 737-742, (2015).
Hauser, et al., "KINECT 3: A Randomised, Double-Blind Placebo-Controlled Phase 3 Trial of Valbenazine (NBI-98854) for Tardive Dyskinesia (PL02.003)", Neurology, (2016), 86(16 Supplement). Abstract.
Hauser, et al., "KINECT 3: A Phase 3 Randomised, Double-Blind Placebo-Controlled Trial of Valbenazine for Tardive Dyskinesia", Am. J. Psychiatry, 174(5), pp. 476-484, (2017).
Ashcroft, et al., "A Comparison of Tetrabenazine and Chlorpromazine in Chronic Schizophrenia", Br. J. Psychiatry, 107(447), pp. 287-293, (1961).
Chen, et al., "Tetrabenazine for the Treatment of Hyperkinetic Movement Disorders: A Review of the Literature", Clin. Ther., 34(7), pp. 1487-1504, (2012).
Shen, et al., "Safety and Efficacy of Tetrabenazine and Use of Concomitant Medications During Long-Term, Open-Label Treatment of Chorea Associated with Huntington's and Other Diseases", Tremor Other Hyperkinet Mov, 3, pp. 1-13., (2013).
Skor, et al., "Differences in Dihydrotetrabenazine Isomer Concentrations Following Administration of Tetrabenazine and Valbenazine", Drugs R&D, 17(3), pp. 449-459, (2017).
"Archive History for NCT02844179 (+)-Alpha-Dihydrotetrabenazine Phase I" U.S. National Library of Medicine, https://clinicaltrials.gov/ct2/history/NCT02844179?V_1=View#StudyPageTop (2016).
Kilbourn, "Rat pancreas uptake of [11C]dihydrotetrabenazine stereoisomers" Nucl. Med. Biol. (2010), 37(8), pp. 869-871.
Boldt et al., "Synthesis of (+)- and (−)Tetrabenazine from the Resolution of [alpha]-Dihydrotetrabenazine", Synth. Commun., (2009), 39(20), pp. 3574-3585.
Walkup, J.T., "A Guide to Tourette Syndrome Medications", https://depts.washington.edu/dbpeds/A%20Guide%20to%20TS%20Medications_M-313.pdf, pp. 1-14 (2008).

PHARMACEUTICAL COMPOSITIONS

CROSS REFERENCE TO RELATED APPLICATIONS

This application is a divisional of U.S. patent application Ser. No. 15/939,826 filed Mar. 29, 2018 which claims priority to Great Britain Application No. 1705303.4, filed on Apr. 1, 2017. The entire contents of each of the prior applications are hereby incorporated herein by reference.

This invention relates to a novel dihydrotetrabenazine salt, pharmaceutical compositions containing it, processes for making it and its therapeutic use, for example in the treatment of hyperkinetic movement disorders such as Tourette's syndrome.

BACKGROUND OF THE INVENTION

Movement disorders can generally be classified into two categories: hyperkinetic movement disorders and hypokinetic movement disorders. Hyperkinetic movement disorders are caused by an increase in muscular activity and can cause abnormal and/or excessive movements, including tremors, dystonia, chorea, tics, myoclonus and stereotypes.

Hyperkinetic movement disorders often are often psychological in nature and arise through improper regulation of amine neurotransmitters in the basal ganglia.

Tourette's syndrome is an inherited neurological condition characterised by multiple physical and vocal tics. The tics are usually repetitive, but random, physical movements or vocal noises. The vocal tics can be of various forms and include repeating one's own words, the words of others or other sounds. Onset usually occurs in children and continues through to adolescence and adulthood.

While the tics associated with Tourette's syndrome are temporarily suppressible, those affected can usually only supress their tics for limited time periods. There is yet to be an effective treatment to cover all types of tics in all patients, but certain medicaments for tic suppression have been developed.

It is known that dopamine receptor antagonists display an ability to supress tics in Tourette's syndrome patients and a number dopamine receptor antagonists are currently used in the suppression of Tourette's tics, such as fluphenazine, risperidone, haloperidol and pimozide.

Type 2 vesicular monoamine transporter (VMAT2) is a membrane protein responsible for the transportation of monoamine neurotransmitters, such as dopamine, serotonin and histamine, from cellular cytosol into synaptic vesicles. Inhibition of this protein hinders presynaptic neurons from releasing dopamine, resulting in a depletion of dopamine levels in the brain.

It is therefore to be expected that VMAT2 inhibitors may be effective agents against the symptoms of Tourette's syndrome.

Tetrabenazine (Chemical name: 1,3,4,6,7,11b-hexahydro-9,10-dimethoxy-3-(2-methylpropyl)-2H-benzo(a)quinolizin-2-one) has been in use as a pharmaceutical drug since the late 1950s. Initially used as an anti-psychotic, tetrabenazine is currently used for treating hyperkinetic movement disorders such as Huntington's disease, hemiballismus, senile chorea, tic, tardive dyskinesia and Tourette's syndrome, see for example Jankovic et al., *Am. J. Psychiatry.* (1999) August; 156(8):1279-81 and Jankovic et al., *Neurology* (1997) February; 48(2):358-62.

The primary pharmacological action of tetrabenazine is to reduce the supply of monoamines (e.g. dopamine, serotonin, and norepinephrine) in the central nervous system by inhibiting the human vesicular monoamine transporter isoform 2 (hVMAT2). The drug also blocks postsynaptic dopamine receptors.

Tetrabenazine is an effective and safe drug for the treatment of a variety of hyperkinetic movement disorders and, in contrast to typical neuroleptics, has not been demonstrated to cause tardive dyskinesia. Nevertheless, tetrabenazine does exhibit a number of dose-related side effects including causing depression, parkinsonism, drowsiness, nervousness or anxiety, insomnia and, in rare cases, neuroleptic malignant syndrome.

The central effects of tetrabenazine closely resemble those of reserpine, but it differs from reserpine in that it lacks activity at the VMAT1 transporter. The lack of activity at the VMAT1 transporter means that tetrabenazine has less peripheral activity than reserpine and consequently does not produce VMAT1-related side effects such as hypotension.

The chemical structure of tetrabenazine is as shown below.

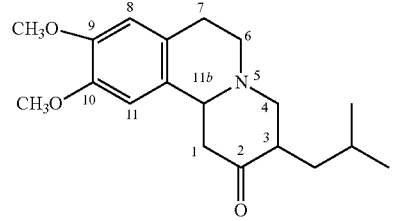

Structure of Tetrabenazine

The compound has chiral centres at the 3 and 11b carbon atoms and hence can, theoretically, exist in a total of four isomeric forms, as shown below.

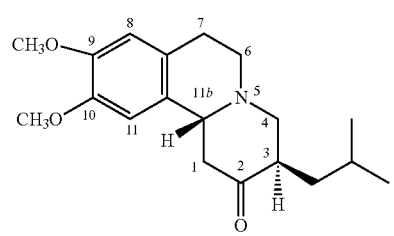

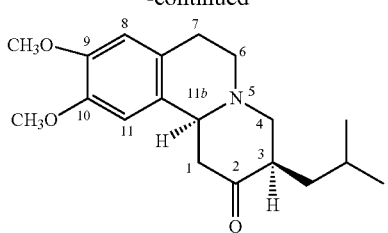

RS

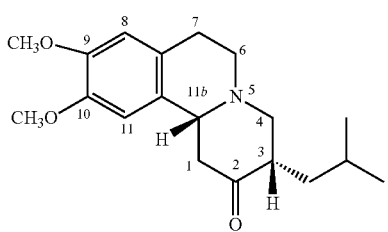

SR

Possible Tetrabenazine Isomers

The stereochemistry of each isomer is defined using the "R and S" nomenclature developed by Cahn, Ingold and Prelog, see *Advanced Organic Chemistry* by Jerry March, 4$^{th}$ Edition, John Wiley & Sons, New York, 1992, pages 109-114. In this patent application, the designations "R" or "S" are given in the order of the position numbers of the carbon atoms. Thus, for example, RS is a shorthand notation for 3R,11bS. Similarly, when three chiral centres are present, as in the dihydrotetrabenazines described below, the designations "R" or "S" are listed in the order of the carbon atoms 2, 3 and 1b. Thus, the 2R,3S,11bS isomer is referred to in short hand form as RSS and so on.

Commercially available tetrabenazine is a racemic mixture of the RR and SS isomers and it would appear that the RR and SS isomers are the most thermodynamically stable isomers.

Tetrabenazine has somewhat poor and variable bioavailability. It is extensively metabolised by first-pass metabolism, and little or no unchanged tetrabenazine is typically detected in the urine. It is known that at least some of the metabolites of tetrabenazine are dihydrotetrabenazines formed by reduction of the 2-keto group in tetrabenazine.

Dihydrotetrabenazine (Chemical name: 2-hydroxy-3-(2-methylpropyl)-1,3,4,6,7,11b-hexahydro-9,10-dimethoxy-benzo(a)quinolizine) has three chiral centres and can therefore exist in any of the following eight optical isomeric forms:

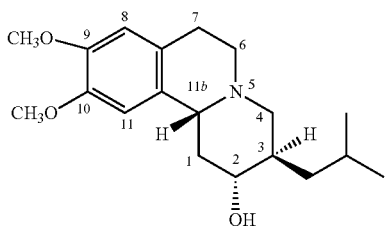

RRR

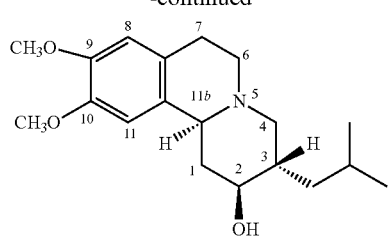

SSS

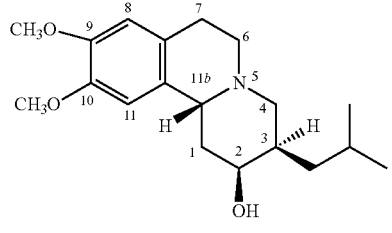

SRR

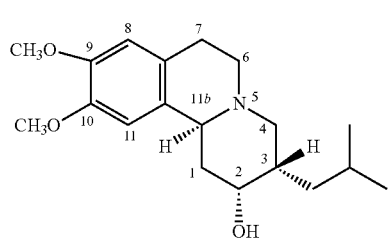

RSS

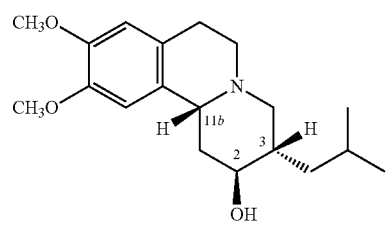

SSR

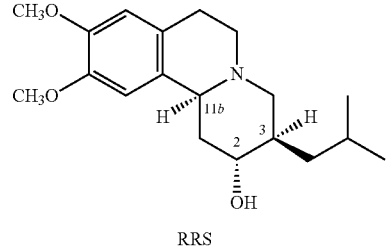

RRS

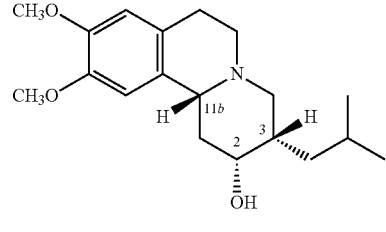

RSR

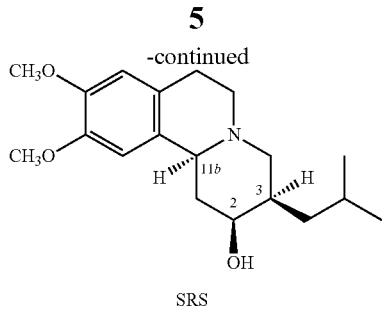

SRS

Dihydrotetrabenazine Isomers

The synthesis and characterisation of all eight dihydrotetrabenazine isomers is described by Sun et al. (*Eur. J. Med. Chem.* (2011), 1841-1848).

Of the eight dihydrotetrabenazine isomers, four isomers are derived from the more stable RR and SS isomers of the parent tetrabenazine, namely the RRR, SSS, SRR and RSS isomers.

The RRR and SSS isomers are commonly referred to as "alpha (α)" dihydrotetrabenazines and can be referred to individually as (+)-α-dihydrotetrabenazine and (−)-α-dihydrotetrabenazine respectively. The alpha isomers are characterised by a trans relative orientation of the hydroxyl and 2-methylpropyl substituents at the 2- and 3-positions—see for example, Kilbourn et al., *Chirality*, 9:59-62 (1997) and Brossi et al., *Helv. Chim. Acta.*, vol. XLI, No. 193, pp 1793-1806 (1958).

The SRR and RSS isomers are commonly referred to as "beta (β)" isomers and can be referred to individually as (+)-β-dihydrotetrabenazine and (−)-β-dihydrotetrabenazine respectively. The beta isomers are characterised by a cis relative orientation of the hydroxyl and 2-methylpropyl substituents at the 2- and 3-positions.

Although dihydrotetrabenazine is believed to be primarily responsible for the activity of the drug, there have been no studies published to date that contain evidence demonstrating which of the various stereoisomers of dihydrotetrabenazine is responsible for its biological activity. More specifically, there have been no published studies demonstrating which of the stereoisomers is responsible for the ability of tetrabenazine to treat movement disorders such as Tourette's syndrome.

Schwartz et al. (*Biochem. Pharmacol.* (1966), 15: 645-655) describes metabolic studies of tetrabenazine carried out in rabbits, dogs and humans. Schwartz et al. identified nine metabolites, five of which were unconjugated and the other four of which were conjugated with glucuronic acid. The five unconjugated metabolites were the alpha- and beta-dihydrotetrabenazines, their two oxidised analogues in which a hydroxyl group has been introduced into the 2-methylpropyl side chain, and oxidised tetrabenazine in which a hydroxyl group has been introduced into the 2-methylpropyl side chain. The four conjugated metabolites were all compounds in which the 9-methoxy group had been demethylated to give a 9-hydroxy compound. The chirality of the various metabolites was not studied and, in particular, there was no disclosure of the chirality of the individual α- and β-isomers.

Scherman et al., (*Mol. Pharmacol.* (1987), 33, 72-77 describes the stereospecificity of VMAT2 binding between racemic α- and β-dihydrotetrabenazine. They reported that α-dihydrotetrabenazine had a 3- to 4-fold higher affinity for the Chromaffin Granule Monoamine Transporter than the β-isomer, when studied in vitro. However, Scherman et al. does not disclose the resolution or testing of the individual enantiomers of the α- and β-dihydrotetrabenazines.

Mehvar et al. (*J. Pharm. Sci.* (1987), 76(6), 461-465) reported a study of the concentrations of tetrabenazine and dihydrotetrabenazine in the brains of rats following administration of either tetrabenazine or dihydrotetrabenazine. The study showed that despite its greater polarity, dihydrotetrabenazine was able to cross the blood-brain barrier. However, the stereochemistry of the dihydrotetrabenazine was not disclosed.

Mehvar et al. (*Drug Metabolism and Disposition* (1987), 15:2, 250-255) describes studies of the pharmacokinetics of tetrabenazine and dihydrotetrabenazine following administration of tetrabenazine to four patients affected by tardive dyskinesia. Oral administration of tetrabenazine resulted in low plasma concentrations of tetrabenazine but relatively high concentrations of dihydrotetrabenazine. However, the stereochemistry of the dihydrotetrabenazine formed in vivo was not reported.

Roberts et al. (*Eur. J. Clin. Pharmacol.* (1986), 29: 703-708) describes the pharmacokinetics of tetrabenazine and its hydroxy-metabolite in patients treated for involuntary movement disorders. Roberts et al. reported that tetrabenazine was extensively metabolised after oral administration resulting in very low plasma concentrations of tetrabenazine but much higher concentrations of a hydroxy-metabolite. Although they did not describe the identity of the hydroxy-metabolites, they suggested that the high plasma concentrations of the hydroxy-metabolites may be therapeutically important (since the metabolites were known to be pharmacologically active) and that, in view of the disclosure in Schwartz et al. (idem), the combination of cis and trans isomers (i.e. beta and alpha isomers) could be more therapeutically important than the parent drug.

Michael Kilbourn and collaborators at the University of Michigan Medical School have published a number of studies relating to the various isomers of dihydrotetrabenazines. In *Med. Chem. Res.* (1994), 5:113-126, Kilbourn et al. describe the use (+/−)-α-[11C]-dihydrotetrabenazine as in vivo imaging agents for VMAT2 binding studies.

In *Eur. J. Pharmacol* (1995) 278, 249-252, Kilbourn et al. reported competition binding studies using [3H]-tetrabenazine to study the in vitro binding affinity of (+)-, (−)-, and (+/−)-α-DHTBZ. The binding assays gave a Ki value of 0.97 nM for (+)-α-dihydrotetrabenazine and 2.2 μM for (−)-α-dihydrotetrabenazine, thereby showing that the (+) alpha isomer has much greater binding affinity for the VMAT2 receptor than the (−) alpha isomer. However, no studies were reported, or conclusions drawn, as to the usefulness of either isomer in the treatment of movement disorders such as Tourette's syndrome.

In *Chirality* (1997) 9:59-62, Kilbourn et al. described studies aimed at identifying the absolute configuration of (+)-α-dihydrotetrabenazine from which they concluded that it has the 2R, 3R, 11bR configuration shown above. They also referred to the Schwartz et al. and Mehvar et al. articles discussed above as indicating that the α- and β-dihydrotetrabenazines are likely to be the pharmacologically active agents in the human brain but they drew no explicit conclusions as to the precise stereochemical identities of the active metabolites of tetrabenazine.

In *Synapse* (2002), 43:188-194, Kilbourn et al. described the use of (+)-α-[11C]-dihydrotetrabenazine as an agent used to measure specific in vivo binding of the VMAT receptor, in "infusion to equilibrium methods". They found that (−)-α-[11C]-dihydrotetrabenazine produced a uniform brain distribution, consistent with the earlier observations that this enantiomer has a low VMAT affinity.

Sun et al. (idem) investigated the VMAT2 binding affinities of all eight dihydrotetrabenazine isomers. They found that all of the dextrorotatory enantiomers exhibited dramatically more potent VMAT2 binding activity than their corresponding laevorotatory enantiomers with the most active (+)-α-isomer being found to be the most active. However, Sun et al. did not carry out any investigations into the relative efficacies of the individual isomers in treating movement disorders such as Tourette's syndrome.

WO2015/120110 (Auspex) describes extended-release formulations that can contain any of a wide variety of different pharmacological agents, including tetrabenazine and dihydrotetrabenazine. However, there are no worked examples of any dihydrotetrabenazine formulations; but only formulations containing tetrabenazine.

WO 2011/153157 (Auspex Pharmaceutical, Inc.) describes deuterated forms of dihydrotetrabenazine. Many deuterated forms of dihydrotetrabenazine are depicted but the application only provides sufficient information to allow a small number of the depicted compounds to be synthesised. Although racemic mixtures of $d_6$-α-dihydrotetrabenazine and $d_6$-α-dihydrotetrabenazine are disclosed, these mixtures were not resolved and the properties of the individual (+) and (−) isomers were not studied. Similarly, WO 2014/047167 (Auspex Pharmaceutical, Inc.) describes a number of deuterated forms of tetrabenazine and its derivatives. Again, the individual (+) and (−) isomers of deuterated forms of α- and β-dihydrotetrabenazine were not separated or studied.

It appears therefore that, up to the present, it remains unclear as to precisely which dihydrotetrabenazine isomers are responsible for the therapeutic properties resulting from the administration of tetrabenazine.

It has also remained somewhat unclear up until now whether (+)-α-dihydrotetrabenazine will provide a therapeutically useful effect in the treatment of movement disorders such as Tourette's syndrome without the accompaniment of unwanted side effects such as those described above. Thus, for example, whereas WO2016/127133 (Neurocrine Biosciences) refers to the Kilbourn et al. article in Chirality (idem) as indicating that (+)-α-dihydrotetrabenazine is the active metabolite of tetrabenazine. WO2016/127133, it also refers to the studies reported in Login et al. (1982), *Ann. Neurology* 12:257-62 and Reches et al., *J. Pharmacol. Exp. Ther.* (1983), 225:515-521 which indicate that tetrabenazine inhibits presynaptic and postsynaptic dopamine receptors in the rat brain. It is suggested in WO2016/127133 that this "off-target" activity of tetrabenazine may be responsible for some of the observed side effects of tetrabenazine.

As discussed above, it is known that tetrabenazine exhibits a number of dose-related side effects including causing depression and parkinsonism (see WO2016/127133). It appears that these side-effects may also be caused by VMAT2 inhibition and that consequently it is difficult to separate the therapeutic effect of tetrabenazine and tetrabenazine-derived compounds from these side-effects (see Miller, "Valbenazine granted breakthrough drug status for treating tardive dyskinesia", Expert Opin. Investig. Drugs (2015), 24(6), pp. 737-742).

In an attempt to avoid or reduce the side-effects associated with tetrabenazine, a valine ester prodrug of (+)-α-dihydrotetrabenazine has been developed, known by its INN name, Valbenazine. The structure of Valbenazine is shown below:

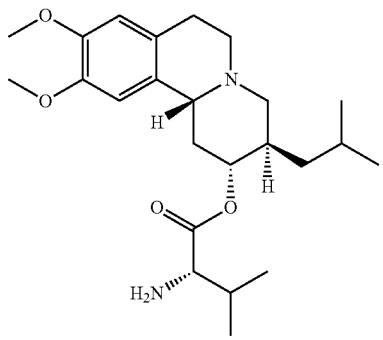 [SMILES: COc1cc2c(cc1OC)[C@H]1C[C@@H](OC(=O)[C@@H](N)C(C)C)[C@H](CC(C)C)CN1CC2]

As disclosed in U.S. Pat. No. 8,039,627, Valbenazine is prepared by reacting (+)-α-dihydrotetrabenazine with carbobenzyloxy-L-valine in dichloromethane and 4-dimethylaminopyridine (DMAP) in the presence of N,N'-dicyclohexylcarbodiimide (DCC) to give the intermediate 2-benzyloxycarbonylamino-3-methyl-butyric acid (2R,3R,1bR)-3-isobutyl-9,10-dimethoxy-1,3,4,6,7,11b-hexahydro-2H-pyrido[2,1-a]isoquinolin-2-yl ester. The intermediate is then hydrogenated over palladium on carbon to remove the benzyloxycarbonyl protecting group to give Valbenazine.

Müller ("Valbenazine granted breakthrough drug status for treating tardive dyskinesia", Expert Opin. Investig. Drugs (2015), 24(6), pp. 737-742) describes a Phase IIb clinical study of Valbenazine ("KINECT 1") in patients suffering from tardive dyskinesia. Although some reduction of symptoms was observed when doses of Valbenazine at 100 mg/day were observed, subjects who received 50 mg/day of Valbenazine did not show any significant signs of improvement, when scored with the abnormal involuntary movement scale (AIMS). Miller concluded that this study was more or less a failure, probably due to low Valbenazine dosing.

In a further study ("KINECT 2") described in the same paper, subjects were initially dosed at 25 mg/day, with the dose range increasing to 75 mg/day. By the end of the study, when measurements were taken, 21 out of 34 of the subjects treated with Valbenazine were being dosed at 75 mg/day (O'Brien et al, "Kinect 2: NBI-98854 treatment of moderate to severe tardive dyskinesia" Mov. Disord. 2014; 29 (Suppl 1):829). The analysis does not provide a breakdown of the reduction in abnormal involuntary movements in patients who were being treated with 75 mg/day by the end of the trial and those who were being treated with 25 mg/day or 50 mg/day by the end of the trial.

A further Phase III trial of Valbenazine, reported by O'Brien et al ("KINECT 3 A randomised, Double-Blind Placebo-Controlled Phase 3 Trial of Valbenazine (NBI-98854) for Tardive Dyskinesia (PL02.003)", Neurology (2016), 86(16), Supplement PL02.003) investigated the change in abnormal involuntary movements in Tardive Dyskinesia sufferers when administered with 40 mg or 80 mg of Valbenazine per day. It was found that 80 mg/day of Valbenazine resulted in a significant improvement in the Abnormal Involuntary Movement Score and it was concluded that 80 mg/day Valbenazine was associated with a significant improvement in Tardive Dyskinesia.

WO 2015/171802 (Neurocrine Biosciences, Inc.) describes methods for treating hyperkinetic diseases by administering therapeutic agents that produce plasma concentrations of (+)-α-dihydrotetrabenazine such that there is a $C_{max}$ of between about 15 ng/ml and 60 ng/ml and a $C_{min}$ of at least 15 ng/ml over an eight hour period. Although it is suggested in WO 2015/171802 that this can be accomplished by administering (+)-α-dihydrotetrabenazine per se, the experiments described in WO 2015/171802 only provide data for (+)-α-dihydrotetrabenazine levels achieved after the administration of Valbenazine. In Example 1 of WO 2015/171802, it is concluded that a concentration of 30 ng/ml of (+)-α-dihydrotetrabenazine in plasma is an appropriate target and that exposures below 15 ng/ml are suboptimal across the general tardive dyskinesia (TD) population. In Example 2 of WO 2015/171802, it is disclosed that a 50 mg dose of Valbenazine appeared to maintain the required plasma levels of (+)-α-dihydrotetrabenazine.

WO2016/210180 (Neurocrine Biosciences) discloses the use of VMAT2 inhibitors for treating various neurological disorders. (+)-α-dihydrotetrabenazine is mentioned as an example of a VMAT2 inhibitor but the VMAT2 inhibitory compounds specifically exemplified in WO2016/210180 are Valbenazine and [(2R, 3S, 11bR)-9,10-dimethoxy-3-(2-methylpropyl)-1H,2H,3H,4H,6H,7H,11bH-pyrido[2,1-a]isoquinolin-2-yl]methanol.

Although having a greater solubility than tetrabenazine, (+)-α-dihydrotetrabenazine still possess a relatively low solubility and also demonstrates a tendency to form polymorphs. Therefore, there exists the need for pharmaceutical compositions of (+)-α-dihydrotetrabenazine with improved physical properties.

THE INVENTION (+)-α-Dihydrotetrabenazine salts are antagonists of VMAT2. Tetrabenazine exerts its therapeutic effects by inhibiting VMAT2 in the brain and by inhibiting both pre-synaptic and post-synaptic dopamine receptors.

The inventors of the present application have found that the (+)-α-dihydrotetrabenazine succinate salt possesses unexpectedly good physical properties in comparison with the free base and other common acid addition salts. In particular, the succinate salt has a higher solubility and a greater thermal stability, with a reduced tendency to form polymorphs, than the free base and other common salts.

On the basis of the studies carried out to date, it is envisaged that the succinate salt of (+)-α-dihydrotetrabenazine will be useful in the prophylaxis or treatment of the disease states and conditions for which tetrabenazine is currently used or proposed. Thus, by way of example, and without limitation, the (+)-α-dihydrotetrabenazine succinate salt of the invention may be used for the treatment of hyperkinetic movement disorders such as Huntington's disease, hemiballismus, senile chorea, tic disorders, tardive dyskinesia, dystonia and Tourette's syndrome. It is also envisaged that the dihydrotetrabenazine succinate salt of the invention may be useful in the treatment of depression.

(+)-α-Dihydrotetrabenazine is believed to have the chemical structure (I) shown in formula (I) below:

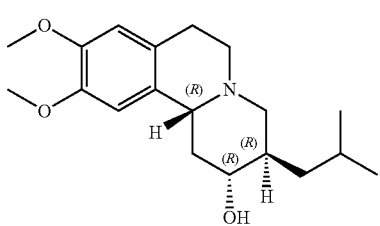

(I)

Accordingly, the invention provides (+)-α-dihydrotetrabenazine succinate, which has a chemical formula as shown in Formula (II).

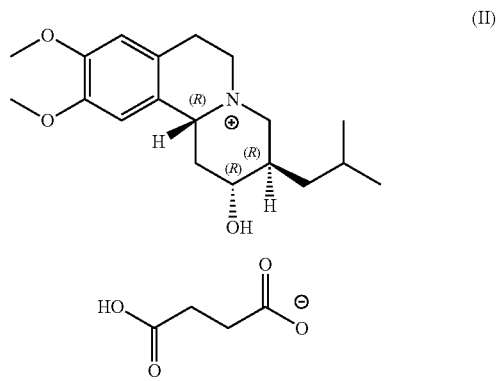

(II)

In this application, (+)-α-dihydrotetrabenazine succinate may be referred to for convenience and brevity as (+)-α-DHTBZ succinate or (+)-α-DHTBZ succinate salt, or the succinate salt of the invention.

The succinate salt of the invention typically has a salt ratio (molar ratio of (+)-α-dihydrotetrabenazine free base to the acid) of approximately 1:1.

In another aspect, the invention provides a pharmaceutical composition comprising (+)-α-dihydrotetrabenazine succinate and a pharmaceutically acceptable excipient.

The invention also provides:
- (+)-α-dihydrotetrabenazine succinate for use in medicine.
- (+)-α-dihydrotetrabenazine succinate for use as a VMAT2 receptor antagonist.
- (+)-α-Dihydrotetrabenazine succinate for use in the treatment of a movement disorder (e.g. a hyperkinetic movement disorder).
- A method of treatment of a movement disorder (e.g. a hyperkinetic movement disorder) in a subject in need thereof (e.g. a mammalian subject such as a human), which method comprises administering to the subject a therapeutically effective amount of (+)-α-dihydrotetrabenazine succinate.
- The use of (+)-α-dihydrotetrabenazine succinate for the manufacture of a medicament for the treatment of a movement disorder (e.g. a hyperkinetic movement disorder).
- A unit dosage form (for example a capsule or a tablet) comprising (+)-α-dihydrotetrabenazine succinate and a pharmaceutically acceptable excipient.

The (+)-α-dihydrotetrabenazine succinate may be used in the treatment of a hyperkinetic movement disorder such as Huntington's disease, hemiballismus, senile chorea, tic disorders, tardive dyskinesia, dystonia and Tourette's syndrome. In one embodiment, the hyperkinetic movement order is Tourette's syndrome.

The (+)-α-dihydrotetrabenazine succinate described herein typically has an isomeric purity of greater than 60%.

The term "isomeric purity" in the present context refers to the amount of (+)-α-dihydrotetrabenazine free base present in the succinate salt relative to the total amount or concentration of dihydrotetrabenazine of all isomeric forms. For example, if 90% of the total dihydrotetrabenazine present in the composition is (+)-α-dihydrotetrabenazine, then the isomeric purity is 90%.

The (+)-α-dihydrotetrabenazine salt of the invention may have an isomeric purity of greater than 82%, greater than 85%, greater than 87%, greater than 90%, greater than 91%, greater than 92%, greater than 93%, greater than 94%, greater than 95%, greater than 96%, greater than 97%, greater than 98%, greater than 99%, greater than 99.5%, or greater than 99.9%.

The (+)-α-dihydrotetrabenazine succinate will generally be administered to a subject in need of such administration, for example a human or animal patient, preferably a human.

The (+)-α-dihydrotetrabenazine succinate will typically be administered in amounts that are therapeutically or prophylactically useful and which generally are non-toxic. However, in certain situations, the benefits of administering a dihydrotetrabenazine compound of the invention may outweigh the disadvantages of any toxic effects or side effects, in which case it may be considered desirable to administer compounds in amounts that are associated with a degree of toxicity.

The inventors of the present application have also found that that (+)-α-dihydrotetrabenazine is effective in the treatment of movement disorders (e.g. a hyperkinetic movement disorder) at much lower doses than could have been predicted from the literature (for example from WO 2015/171802) and that its use at such lower doses can avoid or minimize the unwanted side effects associated with tetrabenazine.

More particularly, experiments carried out by the present inventors indicate that movement disorders such as Tourette's syndrome can be treated effectively by administering much lower doses of (+)-α-dihydrotetrabenazine per se than the doses of Valbenazine required in WO 2015/171802.

Accordingly, in another aspect, the invention provides a pharmaceutical composition comprising (+)-α-dihydrotetrabenazine succinate and a pharmaceutically acceptable excipient.

The pharmaceutical composition can be, for example, a unit dosage form comprising from 0.5 mg to 30 mg (e.g. between 0.5 mg and 20 mg) of (+)-α-dihydrotetrabenazine succinate and a pharmaceutically acceptable excipient.

The unit dosage form can be one which is administered orally, for example a capsule or tablet.

In particular embodiments of the invention, there is provided:

A unit dosage form comprising from 0.5 mg to 30 mg (e.g. between 0.5 mg and 30 mg) of (+)-α-dihydrotetrabenazine succinate and a pharmaceutically acceptable excipient.

A unit dosage form comprising from 0.5 mg to 25 mg (e.g. between 0.5 mg and 25 mg) of (+)-α-dihydrotetrabenazine succinate and a pharmaceutically acceptable excipient.

A unit dosage form comprising from 0.5 mg to 20 mg (e.g. between 0.5 mg and 20 mg) of (+)-α-dihydrotetrabenazine succinate and a pharmaceutically acceptable excipient.

A unit dosage form comprising from 1 mg to 30 mg (e.g. between 1 mg and 30 mg) of (+)-α-dihydrotetrabenazine succinate and a pharmaceutically acceptable excipient.

A unit dosage form comprising from 1 mg to 25 mg (e.g. between 1 mg and 25 mg) of (+)-α-dihydrotetrabenazine succinate and a pharmaceutically acceptable excipient.

A unit dosage form comprising from 1 mg to 20 mg (e.g. between 1 mg and 20 mg) of (+)-α-dihydrotetrabenazine succinate and a pharmaceutically acceptable excipient.

A unit dosage form comprising from 2 mg to 20 mg (e.g. between 2 mg and 20 mg) of (+)-α-dihydrotetrabenazine succinate and a pharmaceutically acceptable excipient.

A unit dosage form comprising from 0.5 mg to 10 mg (e.g. between 0.5 mg and 10 mg) of (+)-α-dihydrotetrabenazine succinate and a pharmaceutically acceptable excipient.

A unit dosage form comprising from 0.5 mg to 7.5 mg (e.g. between 0.5 mg and 7.5 mg) of (+)-α-dihydrotetrabenazine succinate and a pharmaceutically acceptable excipient.

A unit dosage form comprising from 1 mg to 10 mg (e.g. between 1 mg and 10 mg) of (+)-α-dihydrotetrabenazine succinate and a pharmaceutically acceptable excipient.

A unit dosage form comprising from 1 mg to 7.5 mg (e.g. between 1 mg and 7.5 mg) of (+)-α-dihydrotetrabenazine succinate and a pharmaceutically acceptable excipient.

A unit dosage form comprising from 3 mg to 20 mg (e.g. between 3 mg and 20 mg) of (+)-α-dihydrotetrabenazine succinate and a pharmaceutically acceptable excipient.

A unit dosage form comprising from 2 mg to 15 mg (e.g. between 2 mg and 15 mg) of (+)-α-dihydrotetrabenazine succinate and a pharmaceutically acceptable excipient.

A unit dosage form comprising from 3 mg to 15 mg (e.g. between 3 mg and 15 mg) of (+)-α-dihydrotetrabenazine succinate and a pharmaceutically acceptable excipient.

A unit dosage form comprising from 4 mg to 15 mg (e.g. between 4 mg and 15 mg) of (+)-α-dihydrotetrabenazine succinate and a pharmaceutically acceptable excipient.

A unit dosage form comprising from 5 mg to 15 mg (e.g. between 5 mg and 15 mg) of (+)-α-dihydrotetrabenazine succinate and a pharmaceutically acceptable excipient.

A unit dosage form comprising approximately 0.5 mg of (+)-α-dihydrotetrabenazine succinate and a pharmaceutically acceptable excipient.

A unit dosage form comprising approximately 1 mg of (+)-α-dihydrotetrabenazine succinate and a pharmaceutically acceptable excipient.

A unit dosage form comprising approximately 2 mg of (+)-α-dihydrotetrabenazine succinate and a pharmaceutically acceptable excipient.

A unit dosage form comprising approximately 3 mg of (+)-α-dihydrotetrabenazine succinate and a pharmaceutically acceptable excipient.

A unit dosage form comprising approximately 4 mg of (+)-α-dihydrotetrabenazine succinate and a pharmaceutically acceptable excipient.

A unit dosage form comprising approximately 5 mg of (+)-α-dihydrotetrabenazine succinate and a pharmaceutically acceptable excipient.

A unit dosage form comprising approximately 7.5 mg of (+)-α-dihydrotetrabenazine succinate and a pharmaceutically acceptable excipient.

A unit dosage form comprising approximately 10 mg of (+)-α-dihydrotetrabenazine succinate and a pharmaceutically acceptable excipient.

A unit dosage form comprising approximately 12.5 mg of (+)-α-dihydrotetrabenazine succinate and a pharmaceutically acceptable excipient.

A unit dosage form comprising approximately 15 mg of (+)-α-dihydrotetrabenazine succinate and a pharmaceutically acceptable excipient.

The unit dosage forms may be administered orally and may be capsules or tablets.

The unit dosage forms defined and described above are typically for use in the treatment of a hyperkinetic movement disorder such as Huntington's disease, hemiballismus, senile chorea, tic disorders, tardive dyskinesia, dystonia and Tourette's syndrome.

The invention also provides:

(+)-α-dihydrotetrabenazine succinate for use in a method for the treatment of a movement disorder (e.g. a hyperkinetic movement disorder), wherein the treatment comprises administering to a subject an amount of (+)-α-dihydrotetrabenzine succinate between 1 mg and 30 mg per day.

A method of treatment of a movement disorder (e.g. a hyperkinetic movement disorder) in a subject in need thereof (e.g. a mammalian subject such as a human), which treatment comprises administering to the subject an amount of (+)-α-dihydrotetrabenazine succinate between 1 mg and 30 mg per day.

The use of (+)-α-dihydrotetrabenazine succinate for the manufacture of a medicament for the treatment of a movement disorder (e.g. a hyperkinetic movement disorder), which treatment comprises administering to the subject an amount of (+)-α-dihydrotetrabenazine succinate between 1 mg and 30 mg per day.

(+)-α-dihydrotetrabenazine succinate for use, a method or a use as described herein, wherein the treatment comprises administering to the subject an amount of (+)-α-dihydrotetrabenazine succinate between 2 mg and 30 mg per day.

(+)-α-dihydrotetrabenazine succinate for use, a method or a use as described herein, wherein the treatment comprises administering to the subject an amount of (+)-α-dihydrotetrabenazine succinate between 3 mg and 30 mg per day.

(+)-α-dihydrotetrabenazine succinate for use, a method or a use as described herein, wherein the treatment comprises administering to the subject an amount of (+)-α-dihydrotetrabenazine succinate between 2 mg and 20 mg per day.

(+)-α-dihydrotetrabenazine succinate for use, a method or a use as described herein, wherein the treatment comprises administering to the subject an amount of (+)-α-dihydrotetrabenazine succinate between 3 mg and 20 mg per day.

(+)-α-dihydrotetrabenazine succinate for use, a method or a use as described herein, wherein the treatment comprises administering to the subject an amount of (+)-α-dihydrotetrabenazine succinate between 5 mg and 20 mg per day.

(+)-α-dihydrotetrabenazine succinate for use, a method or a use as described herein, wherein the treatment comprises administering to the subject an amount of (+)-α-dihydrotetrabenazine of approximately 7.5 mg per day.

(+)-α-dihydrotetrabenazine succinate for use, a method or a use as described herein, wherein the treatment comprises administering to the subject an amount of (+)-α-dihydrotetrabenazine succinate of approximately 10 mg per day.

(+)-α-dihydrotetrabenazine succinate for use, a method or a use as described herein, wherein the treatment comprises administering to the subject an amount of (+)-α-dihydrotetrabenazine succinate of approximately 12.5 mg per day.

(+)-α-dihydrotetrabenazine succinate for use, a method or a use as described herein, wherein the treatment comprises administering to the subject an amount of (+)-α-dihydrotetrabenazine succinate of approximately 15 mg per day.

(+)-α-dihydrotetrabenazine succinate for use, a method or a use as described herein, wherein the treatment comprises administering to the subject an amount of (+)-α-dihydrotetrabenazine succinate of approximately 20 mg per day.

In each case, the quantity of (+)-α-dihydrotetrabenazine succinate specified may be administered once per day or in several (e.g. two) doses per day.

In some embodiments, the quantity of (+)-α-dihydrotetrabenazine succinate specified is administered once daily.

The administration of (+)-α-dihydrotetrabenazine succinate typically forms part of a chronic treatment regime. The (+)-α-dihydrotetrabenazine succinate may therefore be administered to a patient for a treatment period of at least a week, more usually at least two weeks, or at least a month, and typically longer than a month. Where a patient is shown to respond well to treatment, the period of treatment can be longer than six months and may extend over a period of years.

The chronic treatment regime may involve the administration of the (+)-α-dihydrotetrabenazine succinate every day, or the treatment regime may include days when no (+)-α-dihydrotetrabenazine succinate is administered.

The dosage administered to the subject may vary during the treatment period. For example, the initial dosage may be increased or decreased depending on the subject's response to the treatment. A subject may, for example, be given an initial low dose to test the subject's tolerance towards the (+)-α-dihydrotetrabenazine succinate, and the dosage thereafter increased as necessary up to a maximum daily intake of 30 mg. Alternatively, an initial daily dosage administered to the patient may be selected so as to give an estimated desired degree of VMAT2 blockage, following which a lower maintenance dose may be given for the remainder of the treatment period, with the option of increasing the dosage should the subject's response to the treatment indicate that an increase is necessary.

Thus, the invention also provides a method of treating a movement disorder in a subject in need thereof, and (+)-α-dihydrotetrabenazine succinate for use in the method; which method comprises the steps of:

(a) administering to the subject an initial daily dosage of (+)-α-dihydrotetrabenazine succinate, wherein the initial daily dosage is an amount of (+)-α-dihydrotetrabenazine succinate corresponding to from 0.5 mg to 5 mg of (+)-α-dihydrotetrabenazine free base;

(b) carrying out a clinical evaluation of the subject for efficacy and side effects arising from the treatment;

(c) where the clinical evaluation (b) has established that an increased daily dosage of (+)-α-dihydrotetrabenazine succinate is desirable, administering an increased daily dosage which is greater than the initial daily dosage by an incremental amount of (+)-α-dihydrotetrabenazine succinate thereof corresponding to from 0.5 mg to 5 mg of (+)-α-dihydrotetrabenazine free base; or, where the clinical evaluation has established that an increased daily dosage is not desirable, either maintaining the initial daily dosage, reducing the dosage, or discontinuing the treatment;

(d) where an increased daily dosage has been administered, carrying out a further clinical evaluation of the subject for efficacy and side effects arising from the treatment with the increased daily dosage;

(e) where the further clinical evaluation (d) has established that a further increased daily dosage of (+)-α-dihydrotetrabenazine succinate is desirable, administering a further increased daily dosage which is greater than an immediately preceding daily dosage by an incremental amount of (+)-α-dihydrotetrabenazine succinate corresponding to from 0.5 mg to 5 mg of (+)-α-dihydrotetrabenazine free base; or, where the clinical evaluation has established that a further increased daily dosage is not desirable, maintaining the immediately preceding daily dosage, reducing the immediately preceding dosage or discontinuing the treatment; and (f) optionally repeating steps (d) and (e) as often as desired until an optimum daily dosage is reached.

In particular embodiments of the foregoing method, there are provided:

A method (or (+)-α-dihydrotetrabenazine succinate for use in the method) wherein the initial daily dosage of (+)-α-dihydrotetrabenazine succinate, is an amount corresponding to from 0.5 mg to 3 mg of (+)-α-dihydrotetrabenazine free base.

A method (or (+)-α-dihydrotetrabenazine succinate for use in the method) wherein the initial daily dosage of (+)-α-dihydrotetrabenazine succinate, is an amount corresponding to from 0.5 mg to 2 mg of (+)-α-dihydrotetrabenazine free base.

A method (or (+)-α-dihydrotetrabenazine succinate for use in the method) wherein the initial daily dosage of (+)-α-dihydrotetrabenazine succinate, is an amount corresponding to 0.5 mg, 1 mg, 1.5 mg, or 2 mg of (+)-α-dihydrotetrabenazine free base.

A method (or (+)-α-dihydrotetrabenazine succinate for use in the method) wherein the initial daily dosage of (+)-α-dihydrotetrabenazine succinate, is an amount corresponding to 0.5 mg of (+)-α-dihydrotetrabenazine free base.

A method (or (+)-α-dihydrotetrabenazine succinate for use in the method) wherein the initial daily dosage of (+)-α-dihydrotetrabenazine succinate, is an amount corresponding to 1 mg of (+)-α-dihydrotetrabenazine free base.

A method (or (+)-α-dihydrotetrabenazine succinate for use in the method) wherein the initial daily dosage of (+)-α-dihydrotetrabenazine succinate, is an amount corresponding to 1.5 mg of (+)-α-dihydrotetrabenazine free base.

A method (or (+)-α-dihydrotetrabenazine succinate for use in the method) wherein the initial daily dosage of (+)-α-dihydrotetrabenazine succinate, is an amount corresponding to 2 mg of (+)-α-dihydrotetrabenazine free base.

A method (or (+)-α-dihydrotetrabenazine succinate for use in the method) wherein the increased daily dosage in step (c) is an amount which is greater than the initial daily dosage by an incremental amount of (+)-α-dihydrotetrabenazine succinate corresponding to from 0.5 mg to 3 mg of (+)-α-dihydrotetrabenazine free base.

A method (or (+)-α-dihydrotetrabenazine succinate for use in the method) wherein the increased daily dosage in step (c) is an amount which is greater than the initial daily dosage by an incremental amount of (+)-α-dihydrotetrabenazine succinate corresponding to from 0.5 mg to 2 mg of (+)-α-dihydrotetrabenazine free base.

A method (or (+)-α-dihydrotetrabenazine succinate for use in the method) wherein the increased daily dosage in step (c) is an amount which is greater than the initial daily dosage by an incremental amount of (+)-α-dihydrotetrabenazine succinate corresponding to 0.5 mg, 1 mg, 1.5 mg, or 2 mg of (+)-α-dihydrotetrabenazine free base.

A method (or (+)-α-dihydrotetrabenazine succinate for use in the method) wherein the increased daily dosage in step (c) is an amount which is greater than the initial daily dosage by an incremental amount of (+)-α-dihydrotetrabenazine succinate corresponding to 0.5 mg of (+)-α-dihydrotetrabenazine free base.

A method (or (+)-α-dihydrotetrabenazine succinate for use in the method) wherein the increased daily dosage in step (c) is an amount which is greater than the initial daily dosage by an incremental amount of (+)-α-dihydrotetrabenazine succinate corresponding to 1 mg of (+)-α-dihydrotetrabenazine free base.

A method (or (+)-α-dihydrotetrabenazine succinate for use in the method) wherein the increased daily dosage in step (c) is an amount which is greater than the initial daily dosage by an incremental amount of (+)-α-dihydrotetrabenazine succinate corresponding to 1.5 mg of (+)-α-dihydrotetrabenazine free base.

A method (or (+)-α-dihydrotetrabenazine succinate for use in the method) wherein the increased daily dosage in step (c) is an amount which is greater than the initial daily dosage by an incremental amount of (+)-α-dihydrotetrabenazine succinate corresponding to 2 mg of (+)-α-dihydrotetrabenazine free base.

A method (or (+)-α-dihydrotetrabenazine succinate for use in the method) wherein the further increased daily dosage in step (e) is greater than an immediately preceding daily dosage by an incremental amount of (+)-α-dihydrotetrabenazine succinate corresponding to from 0.5 mg to 3 mg of (+)-α-dihydrotetrabenazine free base.

A method (or (+)-α-dihydrotetrabenazine succinate for use in the method) wherein the further increased daily dosage in step (e) is greater than an immediately preceding daily dosage by an incremental amount of (+)-α-dihydrotetrabenazine succinate corresponding to from 0.5 mg to 2 mg of (+)-α-dihydrotetrabenazine free base.

A method (or (+)-α-dihydrotetrabenazine succinate for use in the method) wherein the further increased daily dosage in step (e) is greater than an immediately preceding daily dosage by an incremental amount of (+)-α-dihydrotetrabenazine succinate corresponding to 0.5 mg, 1 mg, 1.5 mg, or 2 mg of (+)-α-dihydrotetrabenazine free base.

A method (or (+)-α-dihydrotetrabenazine succinate for use in the method) wherein the further increased daily dosage in step (e) is greater than an immediately preceding daily dosage by an incremental amount of (+)-α-dihydrotetrabenazine succinate corresponding to 0.5 mg of (+)-α-dihydrotetrabenazine free base.

A method (or (+)-α-dihydrotetrabenazine succinate for use in the method) wherein the further increased daily dosage in step (e) is greater than an immediately preceding daily dosage by an incremental amount of (+)-α-dihydrotetrabenazine succinate corresponding to 1 mg of (+)-α-dihydrotetrabenazine free base.

A method (or (+)-α-dihydrotetrabenazine succinate for use in the method) wherein the further increased daily dosage in step (e) is greater than an immediately preceding daily dosage by an incremental amount of (+)-α-dihydrotetrabenazine succinate corresponding to 1.5 mg of (+)-α-dihydrotetrabenazine free base.

A method (or (+)-α-dihydrotetrabenazine succinate for use in the method) wherein the further increased daily dosage in step (e) is greater than an immediately preceding daily dosage by an incremental amount of (+)-α-dihydrotetrabenazine succinate corresponding to 2 mg of (+)-α-dihydrotetrabenazine free base.

A method (or (+)-α-dihydrotetrabenazine succinate for use in the method) wherein the treatment comprises the administration of a maximum (e.g. optimized) daily dosage of (+)-α-dihydrotetrabenazine succinate, which is an amount corresponding to no greater than 20 mg of (+)-α-dihydrotetrabenazine free base.

A method (or (+)-α-dihydrotetrabenazine succinate for use in the method) wherein the treatment comprises the administration of a maximum (e.g. optimized) daily dosage of (+)-α-dihydrotetrabenazine succinate, which is an amount corresponding to no greater than 17.5 mg of (+)-α-dihydrotetrabenazine free base.

A method (or (+)-α-dihydrotetrabenazine succinate for use in the method) wherein the treatment comprises the administration of a maximum (e.g. optimized) daily dosage of (+)-α-dihydrotetrabenazine succinate, which is an amount corresponding to no greater than 15 mg of (+)-α-dihydrotetrabenazine free base.

A method (or (+)-α-dihydrotetrabenazine succinate for use in the method) wherein the treatment comprises the administration of a maximum (e.g. optimized) daily dosage of (+)-α-dihydrotetrabenazine succinate, which is an amount corresponding to no greater than 12.5 mg of (+)-α-dihydrotetrabenazine free base.

A method (or (+)-α-dihydrotetrabenazine succinate for use in the method) wherein the treatment comprises the administration of a maximum (e.g. optimized) daily dosage of (+)-α-dihydrotetrabenazine succinate, which is an amount corresponding to no greater than 10 mg of (+)-α-dihydrotetrabenazine free base.

A method (or (+)-α-dihydrotetrabenazine succinate for use in the method) wherein the treatment comprises the administration of a maximum (e.g. optimized) daily dosage of (+)-α-dihydrotetrabenazine succinate, which is an amount corresponding to no greater than 9 mg of (+)-α-dihydrotetrabenazine free base.

A method (or (+)-α-dihydrotetrabenazine succinate for use in the method) wherein the treatment comprises the administration of a maximum (e.g. optimized) daily dosage of (+)-α-dihydrotetrabenazine succinate, which is an amount corresponding to no greater than 8 mg of (+)-α-dihydrotetrabenazine free base.

A method (or (+)-α-dihydrotetrabenazine succinate for use in the method) wherein the treatment comprises the administration of a maximum (e.g. optimized) daily dosage of (+)-α-dihydrotetrabenazine succinate, which is an amount corresponding to no greater than 7.5 mg of (+)-α-dihydrotetrabenazine free base.

A method (or (+)-α-dihydrotetrabenazine succinate for use in the method) wherein the treatment comprises the administration of a maximum (e.g. optimized) daily dosage of (+)-α-dihydrotetrabenazine succinate, which is an amount corresponding to no greater than 7 mg of (+)-α-dihydrotetrabenazine free base.

A method (or (+)-α-dihydrotetrabenazine succinate for use in the method) wherein the treatment comprises the administration of a maximum (e.g. optimized) daily dosage of (+)-α-dihydrotetrabenazine succinate, which is an amount corresponding to no greater than 6 mg of (+)-α-dihydrotetrabenazine free base.

A method (or (+)-α-dihydrotetrabenazine succinate for use in the method) wherein the treatment comprises the administration of a maximum (e.g. optimized) daily dosage of (+)-α-dihydrotetrabenazine succinate, which is an amount corresponding to no greater than 5 mg of (+)-α-dihydrotetrabenazine free base.

A method (or (+)-α-dihydrotetrabenazine succinate for use in the method) wherein the treatment comprises the administration of a maximum (e.g. optimized) daily dosage of (+)-α-dihydrotetrabenazine succinate, which is an amount corresponding to no greater than 4 mg of (+)-α-dihydrotetrabenazine free base.

A method (or (+)-α-dihydrotetrabenazine succinate for use in the method) wherein the treatment comprises the administration of a maximum (e.g. optimized) daily dosage of (+)-α-dihydrotetrabenazine succinate, which is an amount corresponding to no greater than 3 mg of (+)-α-dihydrotetrabenazine free base.

A method (or (+)-α-dihydrotetrabenazine succinate for use in the method) wherein the treatment comprises the administration of a maximum (e.g. optimized) daily dosage of (+)-α-dihydrotetrabenazine succinate, which is an amount corresponding to no greater than 2.5 mg of (+)-α-dihydrotetrabenazine free base.

The quantity of (+)-α-dihydrotetrabenazine succinate required to achieve the desired therapeutic effect may be dependent on the weight of the subject to be treated. The quantities of (+)-α-dihydrotetrabenazine succinate administered to the subject can be expressed as the number of mg/kg, where "mg" refers to the weight of active compound (i.e. the (+)-α-dihydrotetrabenazine free base component of the salt) and "kg" refers to the weight of the subject to be treated. The appropriate dosage amount can therefore be calculated by multiplying the mg/kg amount by the weight of the subject to be treated. Accordingly, the invention also provides:

(+)-α-dihydrotetrabenazine succinate for use in a method for the treatment of a movement disorder, wherein the treatment comprises administering to a subject an amount of (+)-α-dihydrotetrabenazine succinate salt corresponding to between 0.01 mg/kg and 0.5 mg/kg per day of (+)-α-dihydrotetrabenazine free base provided that the total amount of (+)-α-dihydrotetrabenazine succinate administered per day is in the range from 1 mg to 30 mg (e.g. from 1 mg to 20 mg).

A method of treatment of a movement disorder in a subject in need thereof (e.g. a mammalian subject such as a human), which treatment comprises administering to the subject an amount of (+)-α-dihydrotetrabenazine succinate corresponding to between 0.01 mg/kg and 0.5 mg/kg per day of (+)-α-dihydrotetrabenazine free base, provided that the total amount of (+)-α-dihydrotetrabenazine succinate administered per day is in the range from 1 mg to 30 mg (e.g. from 1 mg to 20 mg).

The use of (+)-α-dihydrotetrabenazine succinate for the manufacture of a medicament for the treatment of a movement disorder, which treatment comprises administering to the subject an amount of (+)-α-dihydrotetrabenazine succinate corresponding to between 0.01 mg/kg and 0.5 mg/kg (+)-α-dihydrotetrabenazine free base, provided that the total amount of (+)-α-dihydrotetrabenazine succinate administered per day is in the range from 1 mg to 30 mg (e.g. from 1 mg to 20 mg).

In further embodiments, there is provided:

(+)-α-dihydrotetrabenazine succinate for use, a method or a use as described herein, wherein the treatment comprises administering to the subject an amount of (+)-α-dihydrotetrabenazine succinate corresponding to between 0.01 mg/kg and 0.3 mg/kg of (+)-α-dihydrotetrabenazine free base per day, provided that the total amount of (+)-α-dihydrotetrabenazine succinate administered per day is in the range from 0.5 mg to 20 mg (e.g. 1 mg to 20 mg).

(+)-α-dihydrotetrabenazine succinate for use, a method or a use as described herein, wherein the treatment comprises administering to the subject an amount of (+)-α-dihydrotetrabenazine succinate corresponding to between 0.02 mg/kg and 0.3 mg/kg of (+)-α-dihydrotetrabenazine free base per day, provided that the total amount of (+)-α-dihydrotetrabenazine succinate administered per day is in the range from 0.5 mg to 20 mg (e.g. 1 mg to 20 mg).

(+)-α-dihydrotetrabenazine succinate for use, a method or a use as described herein, wherein the treatment comprises administering to the subject an amount of (+)-α-dihydrotetrabenazine succinate corresponding to between 0.03 mg/kg and 0.3 mg/kg of (+)-α-dihydrotetrabenazine free base, provided that the total amount of (+)-α-dihydrotetrabenazine succinate administered per day is in the range from 0.5 mg to 20 mg (e.g. 1 mg to 20 mg).

(+)-α-dihydrotetrabenazine succinate for use, a method or a use as described herein, wherein the treatment comprises administering to the subject an amount of (+)-α-dihydrotetrabenazine succinate corresponding to between 0.04 mg/kg and 0.3 mg/kg of (+)-α-dihydrotetrabenazine free base, provided that the total amount of (+)-α-dihydrotetrabenazine succinate administered per day is in the range from 0.5 mg to 20 mg (e.g. 1 mg to 20 mg).

(+)-α-dihydrotetrabenazine succinate for use, a method or a use as described herein, wherein the treatment comprises administering to the subject an amount of (+)-α-dihydrotetrabenazine succinate corresponding to between 0.05 mg/kg and 0.3 mg/kg of (+)-α-dihydrotetrabenazine free base, provided that the total amount of (+)-α-dihydrotetrabenazine succinate administered per day is in the range from 0.5 mg to 20 mg (e.g. 1 mg to 20 mg).

(+)-α-dihydrotetrabenazine succinate for use, a method or a use as described herein, wherein the treatment comprises administering to the subject an amount of (+)-α-dihydrotetrabenazine succinate corresponding to between 0.02 mg/kg and 0.2 mg/kg of (+)-α-dihydrotetrabenazine free base per day, provided that the total amount of (+)-α-dihydrotetrabenazine succinate administered per day is in the range from 0.5 mg to 20 mg (e.g. 1 mg to 20 mg).

(+)-α-dihydrotetrabenazine succinate for use, a method or a use as described herein, wherein the treatment comprises administering to the subject an amount of (+)-α-dihydrotetrabenazine succinate corresponding to between 0.03 mg/kg and 0.2 mg/kg of (+)-α-dihydrotetrabenazine free base, provided that the total amount of (+)-α-dihydrotetrabenazine succinate administered per day is in the range from 0.5 mg to 20 mg (e.g. 1 mg to 20 mg).

(+)-α-dihydrotetrabenazine succinate for use, a method or a use as described herein, wherein the treatment comprises administering to the subject an amount of (+)-α-dihydrotetrabenazine succinate corresponding to between 0.04 mg/kg and 0.2 mg/kg of (+)-α-dihydrotetrabenazine free base, provided that the total amount of (+)-α-dihydrotetrabenazine succinate administered per day is in the range from 0.5 mg to 20 mg (e.g. 1 mg to 20 mg).

(+)-α-dihydrotetrabenazine succinate for use, a method or a use as described herein, wherein the treatment comprises administering to the subject an amount of (+)-α-dihydrotetrabenazine succinate corresponding to between 0.05 mg/kg and 0.2 mg/kg of (+)-α-dihydrotetrabenazine free base, provided that the total amount of (+)-α-dihydrotetrabenazine free base administered per day is in the range from 0.5 mg to 20 mg (e.g. 1 mg to 20 mg).

(+)-α-dihydrotetrabenazine succinate for use, a method or a use as described herein, wherein the treatment comprises administering to the subject an amount of (+)-α-dihydrotetrabenazine succinate corresponding to between 0.02 mg/kg and 0.1 mg/kg of (+)-α-dihydrotetrabenazine free base per day, provided that the total amount of (+)-α-dihydrotetrabenazine succinate administered per day is in the range from 0.5 mg to 20 mg (e.g. 1 mg to 20 mg).

(+)-α-dihydrotetrabenazine succinate for use, a method or a use as described herein, wherein the treatment comprises administering to the subject an amount of (+)-α-dihydrotetrabenazine succinate corresponding to between 0.03 mg/kg and 0.1 mg/kg of (+)-α-dihydrotetrabenazine free base, provided that the total amount of (+)-α-dihydrotetrabenazine succinate administered per day is in the range from 0.5 mg to 20 mg (e.g. 1 mg to 20 mg).

(+)-α-dihydrotetrabenazine succinate for use, a method or a use as described herein, wherein the treatment comprises administering to the subject an amount of (+)-α-dihydrotetrabenazine succinate corresponding to between 0.04 mg/kg and 0.1 mg/kg of (+)-α-dihydrotetrabenazine free base, provided that the total amount of (+)-α-dihydrotetrabenazine succinate administered per day is in the range from 0.5 mg to 20 mg (e.g. 1 mg to 20 mg).

(+)-α-dihydrotetrabenazine succinate for use, a method or a use as described herein, wherein the treatment comprises administering to the subject an amount of (+)-α-dihydrotetrabenazine succinate corresponding to between 0.05 mg/kg and 0.1 mg/kg of (+)-α-dihydrotetrabenazine free base, provided that the total amount of (+)-α-dihydrotetrabenazine succinate administered per day is in the range from 0.5 mg to 20 mg (e.g. 1 mg to 20 mg).

(+)-α-dihydrotetrabenazine succinate for use, a method or a use as described herein, wherein the use or method comprises administering to the subject an effective amount of (+)-α-dihydrotetrabenazine succinate wherein:

(i) when the subject has a weight of 30 kg to 50 kg, the said effective amount is a daily amount of (+)-α-dihydrotetrabenazine or a pharmaceutically acceptable salt thereof corresponding to from 2 mg to 7.5 mg of (+)-α-dihydrotetrabenazine free base;

(ii) when the subject has a weight of 50 kg to 75 kg, the said effective amount is a daily amount of (+)-α-dihydrotetrabenazine or a pharmaceutically acceptable salt thereof corresponding to from 5 mg to 10 mg of (+)-α-dihydrotetrabenazine free base;

(iii) when the subject has a weight of 75 kg to 95 kg, the said effective amount is a daily amount of (+)-α-dihydrotetrabenazine or a pharmaceutically acceptable salt thereof corresponding to from 7.5 mg to 15 mg of (+)-α-dihydrotetrabenazine free base; or (iv) when the subject has a weight of greater than 95 kg, the said effective amount is a daily amount of (+)-α-dihydrotetrabenazine or a pharmaceutically acceptable salt thereof corresponding to from 15 mg to 20 mg of (+)-α-dihydrotetrabenazine free base the amount of (+)-α-dihydrotetrabenazine administered per day is from 15 mg to 20 mg.

The present inventors have found that plasma levels of (+)-α-dihydrotetrabenazine required for effective treatment of hyperkinetic movement disorders can be considerably lower than the plasma levels achieved by administration of Valbenazine as described in WO 2015/171802.

Accordingly, in a further aspect, the invention provides:

(+)-α-dihydrotetrabenazine succinate, or a pharmaceutically acceptable salt thereof, for use in a method of treatment of a movement disorder; or A method of treatment of a movement disorder in a subject in need thereof (e.g. a mammalian subject such as a human); or The use of (+)-α-dihydrotetrabenazine succinate for the manufacture of a medicament for the treatment of a movement disorder wherein the treatment comprises administering to a subject a therapeutically effective amount of the (+)-α-dihydrotetrabenazine succinate in an amount sufficient to achieve an average blood plasma $C_{avg}$ concentration of (+)-α-dihydrotetrabenazine free base, where measured over a period of three hours, in the range from 2 ng/ml to 15 ng/ml.

In one embodiment, the invention provides:

(+)-α-dihydrotetrabenazine succinate for use in a method of treatment of a movement; or A method of treatment of a movement disorder in a subject in need thereof (e.g. a mammalian subject such as a human); or The use of (+)-α-dihydrotetrabenazine succinate for the manufacture of a medicament for the treatment of a movement disorder;

wherein the treatment comprises administering to a subject a therapeutically effective amount of the (+)-α-dihydrotetrabenazine succinate in an amount sufficient to achieve an average blood plasma $C_{avg}$ concentration of (+)-α-dihydrotetrabenazine free base, when measured over a period of three hours, in the range from 3 ng/ml to 15 ng/ml.

Complete blocking of the VMAT2 proteins is considered undesirable as this can lead to unwanted side effects, such as Parkinsonism. The present invention provides plasma levels of (+)-α-dihydrotetrabenazine that are sufficient to give effective treatment of movement disorders but do not block the VMAT2 proteins to an extent that causes Parkinsonism and similar side effects. The levels of VMAT2 blocking can be determined by competitive binding studies using Positron Emission Tomography (PET). By co-administering a radioactive ligand with the compound of interest at various concentrations, the proportion of binding sites occupied can be determined (see for example, Matthews et al., "Positron emission tomography molecular imaging for drug development", *Br. J. Clin. Pharmacol.*, 73:2, 175-186). Accordingly, the invention also provides:

(+)-α-dihydrotetrabenazine succinate for use in a method for the treatment of a movement disorder, wherein the treatment comprises administering to a subject an amount of (+)-α-dihydrotetrabenazine succinate sufficient to cause a level of blocking of up to 90% of the VMAT2 proteins in the subject.

A method of treatment of a movement disorder in a subject in need thereof (e.g. a mammalian subject such as a human), which treatment comprises administering to the subject an amount of (+)-α-dihydrotetrabenazine succinate sufficient to cause a level of blocking of up to 90% of the VMAT2 proteins in the subject.

The use of (+)-α-dihydrotetrabenazine succinate for the manufacture of a medicament for the treatment of a movement disorder, which treatment comprises administering to the subject an amount of (+)-α-dihydrotetrabenazine succinate sufficient to cause a level of blocking of up to 90% of the VMAT2 proteins in the subject.

In further embodiments, there is provided:

(+)-α-dihydrotetrabenazine succinate for use, a method or a use as described herein, wherein the treatment comprises administering to the subject an amount of (+)-α-dihydrotetrabenazine succinate sufficient to cause a level of blocking of up to 85% of the VMAT2 proteins in the subject.

(+)-α-dihydrotetrabenazine succinate for use, a method or a use as described herein, wherein the treatment comprises administering to the subject an amount of (+)-α-dihydrotetrabenazine succinate sufficient to cause a level of blocking of up to 80% of the VMAT2 proteins in the subject.

(+)-α-dihydrotetrabenazine succinate for use, a method or a use as described herein, wherein the treatment comprises administering to the subject an amount of (+)-α-dihydrotetrabenazine succinate sufficient to cause a level of blocking of up to 75% of the VMAT2 proteins in the subject.

(+)-α-dihydrotetrabenazine succinate for use, a method or a use as described herein, wherein the treatment comprises administering to the subject an amount of (+)-α-dihydrotetrabenazine succinate sufficient to cause a level of blocking of up to 70% of the VMAT2 proteins in the subject.

(+)-α-dihydrotetrabenazine succinate for use, a method or a use as described herein, wherein the treatment comprises administering to the subject an amount of (+)-α-dihydrotetrabenazine succinate sufficient to cause a level of blocking of from 25% to 85% of the VMAT2 proteins in the subject.

(+)-α-dihydrotetrabenazine succinate for use, a method or a use as described herein, wherein the treatment comprises administering to the subject an amount of (+)-α-dihydrotetrabenazine succinate sufficient to cause a level of blocking of from 30% to 80% of the VMAT2 proteins in the subject.

(+)-α-dihydrotetrabenazine succinate for use, a method or a use as described herein, wherein the treatment comprises administering to the subject an amount of (+)-α-dihydrotetrabenazine succinate sufficient to cause a level of blocking of from 35% to 75% of the VMAT2 proteins in the subject.

(+)-α-dihydrotetrabenazine succinate for use, a method or a use as described herein, wherein the treatment comprises administering to the subject an amount of (+)-α-dihydrotetrabenazine succinate sufficient to cause a level of blocking of from 35% to 70% of the VMAT2 proteins in the subject.

(+)-α-dihydrotetrabenazine succinate for use, a method or a use as described herein, wherein the treatment comprises administering to the subject an amount of (+)-

α-dihydrotetrabenazine succinate sufficient to cause a level of blocking of from 40% to 75% of the VMAT2 proteins in the subject.

(+)-α-dihydrotetrabenazine succinate for use, a method or a use as described herein, wherein the treatment comprises administering to the subject in need thereof, wherein the method comprising administering to a subject an amount of (+)-α-dihydrotetrabenazine succinate sufficient to cause a level of blocking of from 45% to 75% of the VMAT2 proteins in the subject.

(+)-α-dihydrotetrabenazine succinate for use, a method or a use as described herein, wherein the treatment comprises administering to the subject in need thereof, wherein the method comprising administering to a subject an amount of (+)-α-dihydrotetrabenazine succinate sufficient to cause a level of blocking of from 35% to 80% of the VMAT2 proteins in the subject.

(+)-α-dihydrotetrabenazine succinate for use, a method or a use as described herein, wherein the treatment comprises administering to the subject in need thereof, wherein the method comprising administering to a subject an amount of (+)-α-dihydrotetrabenazine succinate sufficient to cause a level of blocking of from 40% to 80% of the VMAT2 proteins in the subject.

(+)-α-dihydrotetrabenazine succinate for use, a method or a use as described herein, wherein the treatment comprises administering to the subject an amount of (+)-α-dihydrotetrabenazine succinate sufficient to cause a level of blocking of from 45% to 80% of the VMAT2 proteins in the subject.

(+)-α-dihydrotetrabenazine succinate for use, a method or a use as described herein, wherein the treatment comprises administering to the subject an amount of (+)-α-dihydrotetrabenazine succinate sufficient to cause a level of blocking of from 50% to 80% of the VMAT2 proteins in the subject.

(+)-α-dihydrotetrabenazine succinate for use, a method or a use as described herein, wherein the treatment comprises administering to the subject an amount of (+)-α-dihydrotetrabenazine succinate sufficient to cause a level of blocking of from 50% to 85% of the VMAT2 proteins in the subject.

(+)-α-dihydrotetrabenazine succinate for use, a method or a use as described herein, wherein the treatment comprises administering to the subject an amount of (+)-α-dihydrotetrabenazine succinate sufficient to cause a level of blocking of from 55% to 80% of the VMAT2 proteins in the subject.

(+)-α-dihydrotetrabenazine succinate for use, a method or a use as described herein, wherein the treatment comprises administering to the subject an amount of (+)-α-dihydrotetrabenazine succinate sufficient to cause a level of blocking of VMAT2 proteins in the subject of between 30% and 70%.

(+)-α-dihydrotetrabenazine succinate for use, a method or a use as described herein, wherein the treatment comprises administering to the subject in need thereof, wherein the method comprising administering to a subject an amount of (+)-α-dihydrotetrabenazine succinate sufficient to cause a blocking level of VMAT2 proteins in the subject of between 30% and 65%.

(+)-α-dihydrotetrabenazine succinate for use, a method or a use as described herein, wherein the treatment comprises administering to the subject in need thereof, wherein the method comprising administering to a subject an amount of (+)-α-dihydrotetrabenazine succinate sufficient to cause a blocking level of VMAT2 proteins in the subject of between 30% and 60%.

(+)-α-dihydrotetrabenazine succinate for use, a method or a use as described herein, wherein the treatment comprises administering to the subject in need thereof, wherein the method comprising administering to a subject an amount of (+)-α-dihydrotetrabenazine succinate sufficient to cause a level blocking of VMAT2 proteins in the subject of between 40% and 80%.

(+)-α-dihydrotetrabenazine succinate for use, a method or a use as described herein, wherein the treatment comprises administering to the subject in need thereof, wherein the method comprising administering to a subject an amount of (+)-α-dihydrotetrabenazine succinate sufficient to cause a level of blocking of VMAT2 proteins in the subject of between 40% and 75%.

(+)-α-dihydrotetrabenazine succinate for use, a method or a use as described herein, wherein the treatment comprises administering to the subject in need thereof, wherein the method comprising administering to a subject an amount of (+)-α-dihydrotetrabenazine succinate sufficient to cause a level of blocking of VMAT2 proteins in the subject of between 40% and 70%.

(+)-α-dihydrotetrabenazine succinate for use, a method or a use as described herein, wherein the treatment comprises administering to the subject in need thereof, wherein the method comprising administering to a subject an amount of (+)-α-dihydrotetrabenazine succinate sufficient to cause a level of blocking of VMAT2 proteins in the subject of between 40% and 65%.

(+)-α-dihydrotetrabenazine succinate for use, a method or a use as described herein, wherein the treatment comprises administering to the subject in need thereof, wherein the method comprising administering to a subject an amount of (+)-α-dihydrotetrabenazine succinate sufficient to cause a level of blocking of VMAT2 in the subject of between 40% and 60%.

In each of the foregoing aspects and embodiments of the invention, the (+)-α-dihydrotetrabenazine succinate is typically not administered in combination with a therapeutically effective amount of amantadine. More particularly, in each of the foregoing aspects and embodiments of the invention, the (+)-α-dihydrotetrabenazine or pharmaceutically acceptable salt thereof is typically not administered in combination with any amount of amantadine.

The movement disorder can be a hyperkinetic movement disorder such as Huntington's disease, hemiballismus, senile chorea, tic disorders, tardive dyskinesia, dystonia, myoclonus and Tourette's syndrome. In one Embodiment, the movement disorder is Tourette's syndrome. In another embodiment, the movement disorder is tardive dyskinesia. In another embodiment, the movement disorder is Huntington's disease.

The term "treatment" as used herein in the context of treating a condition or disorder, pertains generally to treatment and therapy in which some desired therapeutic effect is achieved, for example, the inhibition of the progress of the condition, and includes a reduction in the rate of progress, a halt in the rate of progress, amelioration of the condition, diminishment or alleviation of at least one symptom associated or caused by the condition being treated and cure of the condition. When the hyperkinetic movement disorder being treated is Tourette's Syndrome, treatment of the disorder may pertain to a reduction of the incidence or severity of tics.

Isotopes

The (+)-α-dihydrotetrabenazine succinate may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{11}C$, $^{12}C$, $^{13}C$ and $^{14}C$ and $^{16}O$ and $^{18}O$.

Typically, the (+)-α-dihydrotetrabenazine succinate of the invention does not contain isotopes (such as $^{11}C$ or $^3H$) in amounts higher than their natural abundance.

In one embodiment, the percentage of the total hydrogen atoms in the (+)-α-dihydrotetrabenazine succinate that are deuterium atoms is less than 2%, more typically less than 1%, more usually less than 0.1%, preferably less than 0.05% and most preferably no more than 0.02%.

In an analogous manner, a reference to a particular functional group also includes within its scope isotopic variations, unless the context indicates otherwise.

The isotopes may be radioactive or non-radioactive. In one embodiment of the invention, the (+)-α-dihydrotetrabenazine succinate contains no radioactive isotopes. Such compounds are preferred for therapeutic use. In another embodiment, however, the (+)-α-dihydrotetrabenazine succinate may contain one or more radioisotopes. Compounds containing such radioisotopes may be useful in a diagnostic context.

Solvates (+)-α-Dihydrotetrabenazine succinate may form solvates.

Examples of solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particular solvates are hydrates, and particular examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the (+)α-dihydrotetrabenazine succinate of the invention may be anhydrous. Therefore, in another embodiment, the (+)-α-dihydrotetrabenazine succinate is in an anhydrous form.

Methods for the Preparation of Dihydrotetrabenazine Succinate Salts (+)-α-Dihydrotetrabenazine (compound of formula (I)) can be prepared from tetrabenazine according to the synthetic route shown in Scheme 1.

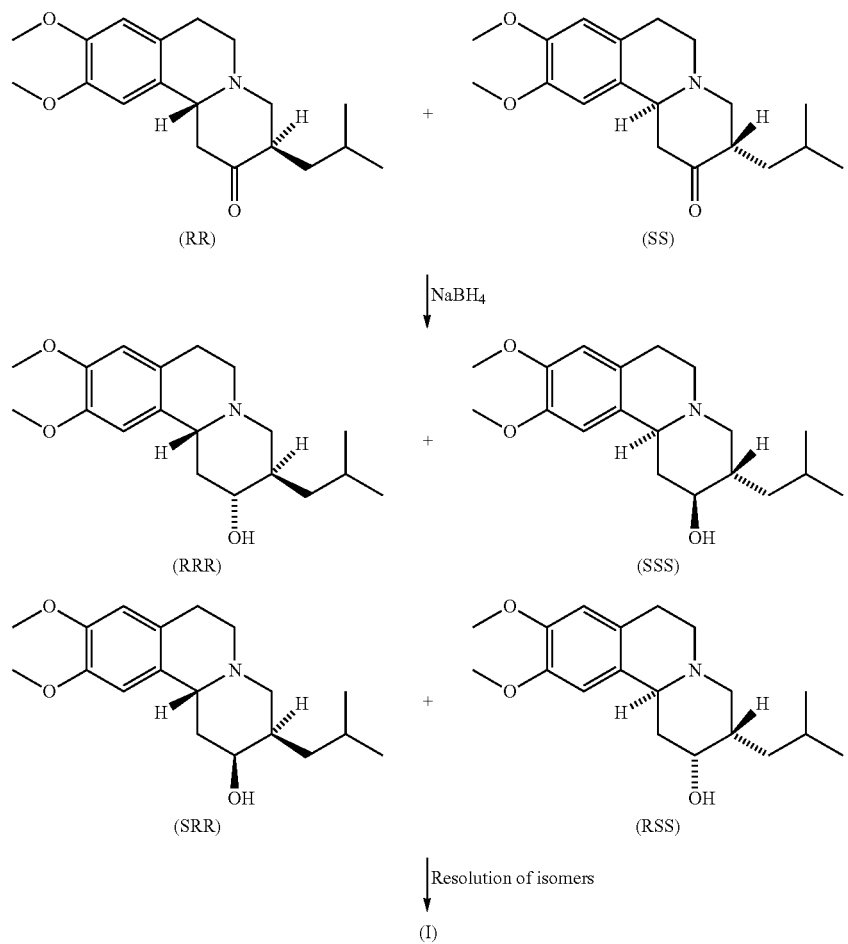

Scheme 1

Racemic tetrabenazine (3-isobutyl-9,10-dimethyoxy-1,3,4,6,7,11b-hexahydro-2H-pyrido[2,1,a]isoquinolin-2-one) containing the RR and SS isomers of tetrabenazine is reduced with sodium borohydride to afford a mixture of four dihydrotetrabenazine isomers of which a racemic mixture of the α-dihydrotetrabenazines (RRR and SSS isomers) constitutes the major product and a racemic mixture of the β-dihydrotetrabenazines (the SRR and RSS isomers) constitutes a minor product. The β-dihydrotetrabenazines can be removed during an initial purification procedure, for example by chromatography or recrystallization and then the racemic α-dihydrotetrabenazines resolved (e.g. by recrystallisation with di-p-toluoyl-L-tartaric acid or (R)-(−)-camphorsulfonic acid or by chiral chromatography), to afford (+)-α-dihydrotetrabenazine (I) ((2R, 3R, 11bR)-3-isobutyl-9,10-dimethoxy-1,3,4,6,7,11b-hexahydro-2H-pyrido[2,1,a]isoquinolin-2-ol).

(+)-α-Dihydrotetrabenazine can also be prepared according to Yao et al., "Preparation and evaluation of tetrabenazine enantiomers and all eight stereoisomers of dihydrotetrabenazine as VMAT2 inhibitors", Eur. J. Med. Chem., (2011), 46, pp. 1841-1848.

The (+)-α-dihydrotetrabenazine succinate salt can then be prepared by reacting the (+)-α-DHTBZ free base with succinic acid. The reaction is typically carried out in the presence of a solvent.

Accordingly, in a further aspect of the invention, there is provided a process for preparing a (+)-α-dihydrotetrabenazine succinate salt of the invention, which process comprises mixing (+)-α-dihydrotetrabenazine free base of the formula (I):

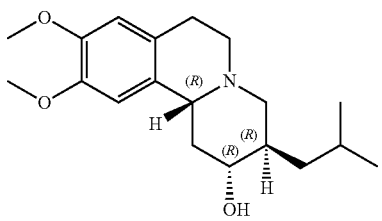

(I)

with succinic acid together with a solvent, allowing formation of the salt to take place, and isolating the (+)-α-dihydrotetrabenazine succinate salt.

In one embodiment, the process for preparing (+)-alpha-DHTBZ succinate salt comprises reacting the (+)-alpha-DHTBZ free base of Formula (II) and succinic acid together with a solvent to form a reaction mixture and then stirring the reaction mixture for a period of at least one hour, more typically at least 2 hours, or at least 4 hours, or at least 12 hours, for example at least 1 day.

The solvent may be a single solvent or may comprise a mixture of solvents. Generally the solvent will consist of or contain at least one polar aprotic solvent, examples being acetone and ethyl acetate.

In one embodiment, the solvent is selected from acetone, ethyl acetate and mixtures thereof.

In a particular embodiment, the solvent is acetone.

A preferred method of preparing (+)-α-dihydrotetrabenazine succinate salt comprises forming a slurry from (+)-α-dihydrotetrabenazine, succinic acid (e.g. at room temperature) and a non-aqueous solvent and stirring the slurry for a time period long enough to permit formation of the succinate salt. The time period is typically at least four hours, more usually at least six hours, or at least twelve hours, and in particular at least eighteen hours. A particular non-aqueous solvent for use in this method is acetone.

Pharmaceutical Formulations and Methods of Treatment

The pharmaceutical compositions of the invention can be in any form suitable for oral, parenteral, topical, intranasal, intrabronchial, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

Pharmaceutical dosage forms suitable for oral administration include tablets, capsules, caplets, pills, lozenges, syrups, solutions, sprays, powders, granules, elixirs and suspensions, sublingual tablets, sprays, wafers or patches and buccal patches.

Pharmaceutical compositions containing (+)-α-dihydrotetrabenazine succinate can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, e.g.; lactose, sucrose, sorbitol or mannitol; and/or a non-sugar derived diluent such as sodium carbonate, calcium phosphate, talc, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethyl-cellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g.; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection. Examples of formulations for rectal or intra-vaginal administration include pessaries and suppositories which may be, for example, formed from a shaped mouldable or waxy material containing the active compound.

Compositions for administration by inhalation may take the form of inhalable powder compositions or liquid or powder sprays, and can be administered in standard form using powder inhaler devices or aerosol dispensing devices. Such devices are well known. For administration by inhalation, the powdered formulations typically comprise the active compound together with an inert solid powdered diluent such as lactose.

Compositions for administration by inhalation may take the form of inhalable powder compositions or liquid or powder sprays, and can be administered in standard form using powder inhaler devices or aerosol dispensing devices. Such devices are well known. For administration by inhalation, the powdered formulations typically comprise the active compound together with an inert solid powdered diluent such as lactose.

Particular pharmaceutical compositions of the invention are compositions selected from:
  Sublingual compositions;
  Intranasal;
  Pellets or tablets formulated to provide release kinetics corresponding to zero order release of the active compound;
  Pellets or tablets formulated to provide first fast release followed by constant rate release (zero order) of the active compound;
  Pellets or tablets formulated to provide a mixture of first order and zero order release of the active compound; and
  Pellets or tablets formulated to provide a combination of zero order and first order release of the active compound; and optionally a further order of release of the active compound selected from second, third and fourth orders of release and combinations thereof.

Pellets and tablets formulated to provide release kinetics of the types defined above can be prepared according to methods well known the skilled person; for example as described in Remington's Pharmaceutical Sciences (idem) and "Remington—The Science and Practice of Pharmacy, 21$^{st}$ edition, 2006, ISBN 0-7817-4673-6.

The compounds of the invention will generally be presented in unit dosage form and, as such, will typically contain an amount of compound sufficient to provide a desired level of biological activity. Such amounts are set out above.

The active compound will be administered to a subject (patient) in need thereof (for example a human or animal patient) in an amount sufficient to achieve the desired therapeutic effect, as described above.

EXAMPLES

Figure 1:
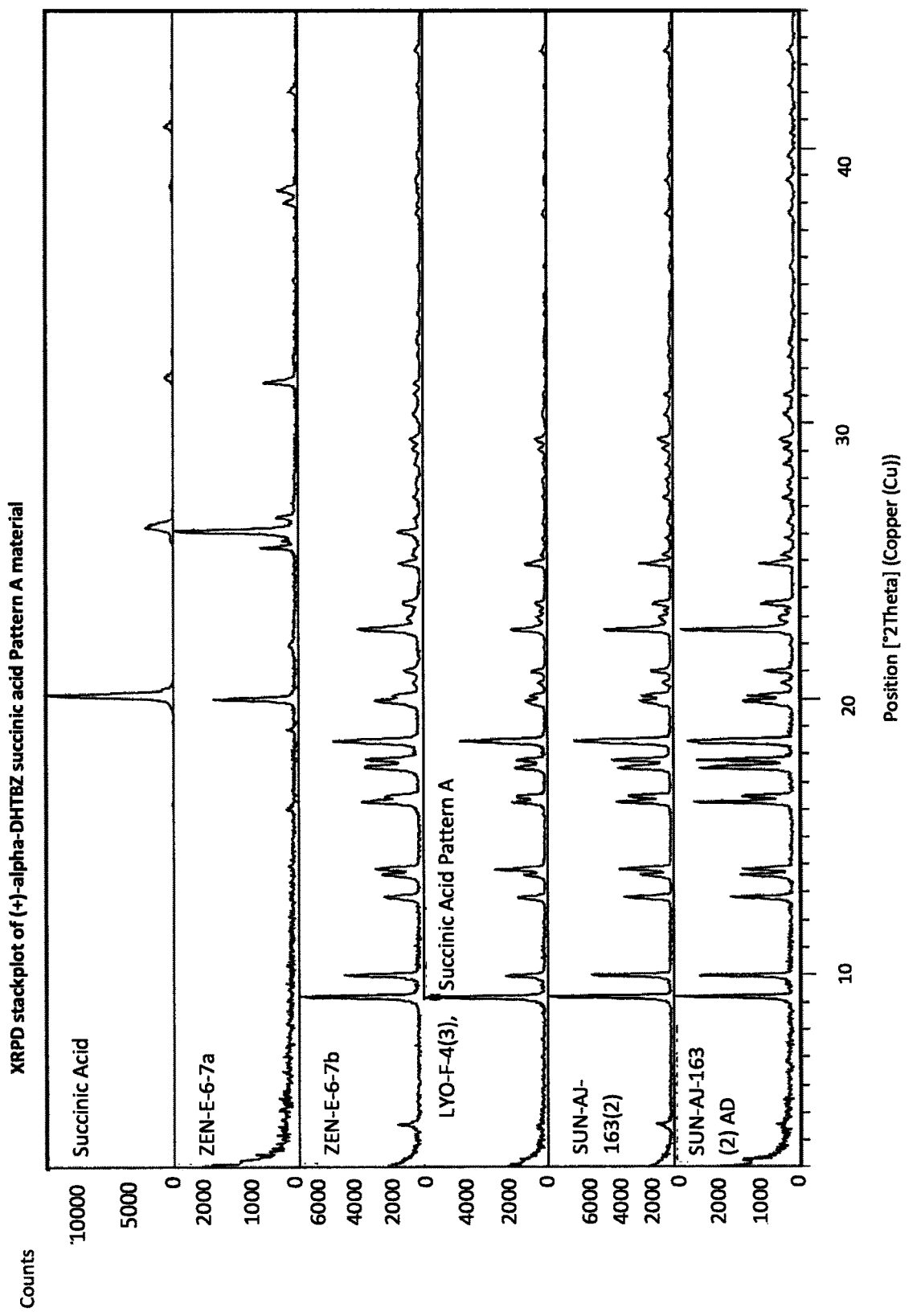
FIG. 1 is a stackplot showing the XRPD patterns for various batches of (+)-α-dihydrotetrabenazine succinate salt together with the XRPD pattern for succinic acid and the XRPD pattern for a solid obtained from a failed attempt to produce the succinate salt.

The following non-limiting examples illustrate the synthesis and properties of salts of (+)-alpha-dihydrotetrabenazine.

Materials and Methods

X-ray powder diffraction (XRPD) studies were carried out using a CubiX-Pro apparatus. XRPD analysis was carried out on the sample "as is". Each sample was placed on a Si zero-return ultra-micro sample holder. Analysis was performed using a 10 mm irradiated width, and the following parameters were set within the hardware/software:
X-ray tube: Cu KV, 45 kV, 40 mA
Detector: X'Celerator
ASS primary slit: Fixed 1°
Divergence slit (Prog): Automatic—5 mm irradiated length
Soller slits: 0.02 radian
Scatter slit (PASS): Automatic—5 mm observed length
Scan range: 3.0-45.0°
Scan mode: Continuous Step size: 0.02°

Time per step: 10 seconds

Active length: 2.54°

$^1$H NMR studies were carried out using a Bruker 500 MHz AVANCE apparatus. The sample was dissolved in DMSO-$d_6$ with 0.05% tetramethylsilane (TMS) as an internal reference. the $^1$H NMR spectrum was recorded at 500 MHz using a 55 mm broadband ($^1$H-X) Z gradient probe. A 30 degree pulse with 20 ppm spectral width, 1.0 second repetition rate, and 32 transients were used in acquiring the spectrum.

Differential scanning calorimetry (DSC) was carried out on the sample "as is" using a Mettler DSC1 instrument. The sample was weighed I an aluminium pan, covered with a pierced lid, and then crimped and analysed from 30-300° C. at 10° C./minute.

Thermal gravimetric analysis was performed on the sample "as is" using a Mettler 851$^e$ TGA instrument. The sample was weighed in an alumina crucible and analysed from 30-300° C. at 10° C./minute.

Moisture-sorption analysis was carried out using a Hiden IGA Sorp moisture-sorption analyser. The analysis was carried out by first holding the sample at 40% relative humidity and 25° C. until an equilibrium weight was reached, or for a maximum of four hours. The sample was then subjected to an isothermal (at 25° C.) adsorption scan from 40 to 90% relative humidity in steps of 10%. The sample was allowed to equilibrate to an asymptotic weight at each point for a maximum of four hours. Following adsorption, a desorption scan from 85 to 5% relative humidity (at 25° C.) was run in steps of 10%, again allowing for a maximum of four hours to an asymptotic weight. An adsorption scan was then performed from 0 to 40% relative humidity inn steps of 10%. The sample was dried for two hours at 60° C. and 0% relative humidity, and the resulting solid was analysed by XRPD.

The aqueous solubilities of salts were measured by an equilibrium method in which an amount of the salt was weighed into a 2 ml vial equipped with a magnetic stirrer bar and water added. In cases where complete dissolution was observed, more material was added until the sample was exhausted. The slurry was then stirred for seven days before isolating the solids by centrifuge-filtration. The solids were analysed by XRPD and the filtrates were analysed by HPLC to determine the amount of (+)-alpha-dihydrotetrabenazine salt in solution. The solubilities were calculated against a calibration curve established for a (+)-alpha-dihydrotetrabenazine sample of known concentration.

The HPLC system used was as follows:

| | |
|---|---|
| System: | Agilent 100 Series HPLC |
| Column: | Phenomenex (Prodigy ODS3, 5 μm, 4.6 × 250 mm |
| Mobile phase A: | 10 mM ammonium acetate (pH 8.0) |
| Mobile phase B: | 9:1 (v/v) acetonitrile/10 mM 10 mM ammonium acetate (pH 8.0) |
| Diluent: | 1:1 (v/v) acetonitrile/water |
| DAD detector: | 235 nm |
| Injection volume: | 10 μL (2-12 μL for calibration curve) |
| Flow rate: | 1.0 mL/minute |
| Column temperature: | 25° |
| Auto sampler temperature: | Ambient |
| Run time: | 40.1 minutes |
| Post-run time: | 5 minutes |

| Gradient: | | |
|---|---|---|
| Time (minutes) | % MP A | % MP B |
| 0 | 90 | 10 |
| 30 | 30 | 70 |
| 35 | 10 | 90 |
| 40 | 10 | 90 |
| 40.1 | 90 | 10 |

Example 1

An Investigation into the Ability of 2R,3R,11bR-Dihydrotetrabenazine to Form Salts Experiments were carried out to assess the ability of (+)-α-dihydrotetrabenazine to form acid addition salts from a variety of mineral and organic acids. More specifically, attempts were made to prepare salts of (+)-α-dihydrotetrabenazine with hydrochloric acid, sulphuric acid, phosphoric acid, L-tartaric acid, citric acid, L-malic acid, adipic acid, methanesulphonic acid, succinic acid, benzenesulphonic acid and naphthalenesulphonic acid. In a first experiment, solutions of (+)-α-dihydrotetrabenazine (32 mg/ml) in either ethyl acetate or acetone were prepared and divided into 1 ml aliquots, each of which was introduced into a 4 ml glass vial equipped with a stirrer bar and the temperature of the solution maintained at 50° C. using a J-KEM heating block. An acid (1.05 molar equivalents) dissolved in dioxane or aqueous dioxane was then added in a dropwise manner. Following addition of the acid, the resulting mixture was gradually cooled to room temperature at a cooling rate of 20° C./hour. Once cooled, the solutions were stirred overnight. Any solids that had formed after this time were separated by centrifuge filtration. Solutions that remained clear were evaporated down to give a residue. In the great majority of cases, the residues were oils. Solids, whether obtained by filtration or by evaporation of solvent, were examined for crystallinity using XRPD. In this experiment, crystalline hydrochloric acid salts were obtained from both ethyl acetate and acetone solutions of (+)-α-dihydrotetrabenazine, and a crystalline benzenesulphonate salt was obtained from an ethyl acetate solution of the (+)-α-DHTBZ. An amorphous phosphoric acid salt was obtained from both ethyl acetate and acetone solutions. The succinic acid-containing vial deposited a solid which, when filtered and analysed by XRPD, proved to be succinic acid rather than a succinate salt of (+)-α-dihydrotetrabenazine In a second experiment, oils and amorphous solids obtained in the first experiment were mixed with 0.5 ml of acetonitrile and stirred for three days at room temperature before filtering off any solids or evaporating clear solutions to give either a solid or oil residue. All solids obtained in this second experiment were tested for crystallinity by XRPD.

In this second experiment, crystalline sulphate and partly crystalline naphthalene-2-sulphonic acid salts were obtained along with a mostly amorphous phosphoric acid salt. As in the first experiment, the succinic acid-containing vial deposited a solid which, when filtered and analysed by XRPD (see FIG. 1 plot ZEN-E-6-7a), provided to be succinic acid (see FIG. 1 plot Succinic acid) rather than a succinate salt of (+)-α-dihydrotetrabenazine.

In a third experiment, to each of the vials from the second experiment that contained L-tartaric acid, succinic acid, citric acid, L-malic acid, adipic acid and methanesulphonic acid was added 0.5 ml of ethyl acetate and the resulting mixtures were stirred for ten days at room temperatures. At the end of this period, any slurries were either filtered or subjected to decanting and any clear solutions were evaporated to dryness under a gentle stream of nitrogen. This experiment produced crystalline (+)-α-dihydrotetrabenazine succinate salt which was filtered off, dried under vacuum and then subjected to XRPD analysis to confirm its crystallinity (see FIG. 1 plot ZEN-E-6-7b).

The foregoing experiments demonstrate the difficulty in forming acid addition salts of (+)-α-dihydrotetrabenazine. Thus, of the free base/acid combinations tested, only succinic acid, hydrochloric acid, sulphuric acid, benzenesulphonic acid, and naphthalene-2-sulphonic acids formed crystalline salts with (+)-α-dihydrotetrabenazine. The naphthalene-2-sulphonic acid salt was, however, gummy, brown and somewhat difficult to handle. A solid material was obtained by reaction with phosphoric acid but this was amorphous.

Example 2

Further Characterisation of (+)-α-Dihydrotetrabenazine Salts

Based on the studies described in Example 1, the succinic acid, hydrochloric acid, sulphuric acid and benzenesulphonic acid salts were selected for further characterisation.

2A. Hydrochloride Salt Form A (+)-α-Dihydrotetrabenazine free base (30 mg) was dissolved in acetone (1 ml) at 50° C. in an 8 ml vial and 0.225 ml of a 0.5M solution of hydrochloric acid in either water or a 1:7 dioxane:water mixture (corresponding to 1.1 molar equivalents relative to the free base) was added dropwise with stirring to the vial. The vial was cooled slowly to ambient temperature and stirred overnight. The resulting solution was then evaporated to dryness under a gentle stream of nitrogen. Acetonitrile (0.5 ml) was added and the mixture was stirred to form a slurry. After three days of stirring, the resulting solids were isolated by centrifuge-filtration and dried at ambient temperature under reduced pressure to give (+)-α-dihydrotetrabenazine hydrochloride crystalline form A, the crystallinity of which was confirmed by XRPD analysis.

The $^1$H NMR spectrum of (+)-α-dihydrotetrabenazine hydrochloride crystalline form A is consistent with that of the free base. The salt ratio was found to be 0.95:1. Crystalline HCl salt form A was subjected to DSC analysis and showed endotherms at 245° C. and 283° C. No weight loss was observed by TGA analysis. Thus, the HCl salt form A has good thermal stability.

The equilibrium solubility of HCl salt form A was determined by HPLC and was found to be 203 mg/mol.

2B. Hydrochloride Salt Form B

When HCl salt form A was stirred in an aqueous slurry for one week conversion to a different (by XRPD) crystalline form (salt form B) took place. Salt form B was found to have a salt ratio of 0.83:1. DSC analysis showed endotherms at 96° C., 114° C. and 246° C. and a single exotherm at 165° C. TGA analysis showed a 1.2% loss in weight. The data indicated that salt form B is a hydrate. This salt form was not characterised further due to its undesirable thermal behaviour.

2C. Sulphate Salt (+)-α-Dihydrotetrabenazine free base (300 mg) was dissolved in ethyl acetate (10 ml) at 50° C. and 2.190 ml of a 0.50M solution of sulphuric acid in 3:1 dioxane:water (corresponding to 1.1 molar equivalents) was added dropwise with stirring to the solution of free base. The solution was then cooled slowly (at a rate of 20° C. per hour) to room temperature and stirred overnight. The clear solution was then evaporated to dryness under a gentle stream of nitrogen. Acetonitrile (5 ml) was added to the residue and the resulting slurry was stirred for three days. The solids were then isolated by centrifuge filtration and dried at ambient temperature under reduced pressure to give the sulphate salt as a crystalline solid, the crystallinity of which was confirmed by XRPD.

DSC analysis of the sulphate salt showed endotherms at 209° C. and 279° C. and a single exotherm at 223° C. TGA analysis showed a 3.7% weight loss.

The salt ratio for the sulphate salt was found to vary from batch to batch. In one batch, a salt ratio of 0.67:1 was obtained while in another batch the salt had a salt ratio of only 0.27:1. Because of the variability of the salt ratio, the sulphate salt was not characterised further.

2D. Benzenesulphonate Salt (+)-α-Dihydrotetrabenazine free base (300 mg) was dissolved in acetone (10 ml) at 50° C. and 2.10 ml of a 0.50M solution of benzenesulphonic acid in dioxane (corresponding to 1.1 molar equivalents) was added dropwise with stirring to the solution of free base. The solution was then cooled slowly (at a rate of 20° C. per hour) to room temperature and stirred overnight. The resulting solids were then isolated by centrifuge filtration and dried at ambient temperature under reduced pressure to give the benzenesulphonate salt as a crystalline solid, the crystallinity of which was confirmed by XRPD.

The salt ratio was analysed by NMR and the 1H NMR spectrum was found to be consistent with was found to be 1.1:1. DSC analysis showed a single endotherm at 249° C. No weight loss was observed by TGA analysis. In gravimetric moisture-sorption studies, the salt was observed to be slightly hygroscopic, moisture uptake of 0.2 wt % being observed at 60% relative humidity and 1.7 wt % moisture uptake being observed at 90% relative humidity.

The benzenesulphonate salt remained unchanged (according to XRPD analysis) after one week of stirring in a water, ethanol and ethyl acetate slurry.

The equilibrium solubility of the benzenesulphonate salt was found to be 2.20 mg/ml by HPLC studies.

2E. Preparation of (+)-α-Dihydrotetrabenazine Succinate Salt (+)-α-Dihydrotetrabenazine free base (313 mg) and succinic acid (116 mg, 1.0 Molar equivalent) were introduced in the solid state into a 20 mL vial equipped with a magnetic stirrer bar. Acetone (1.0 ml) was added and the resulting slurry was stirred for 4 days at room temperature before filtering to afford the (+)-α-dihydrotetrabenazine succinate salt.

The succinate salt was characterised by X-Ray Powder Diffraction (XRPD), $^1$H NMR, Differential Scanning Calorimetry (DSC) and Thermogravimetric Analysis (TGA).

The XRPD pattern for the salt is shown in FIG. 1 (see plot SUN-A-J-163(2)). The XRPD pattern illustrates that the salt is crystalline.

Figure 2:
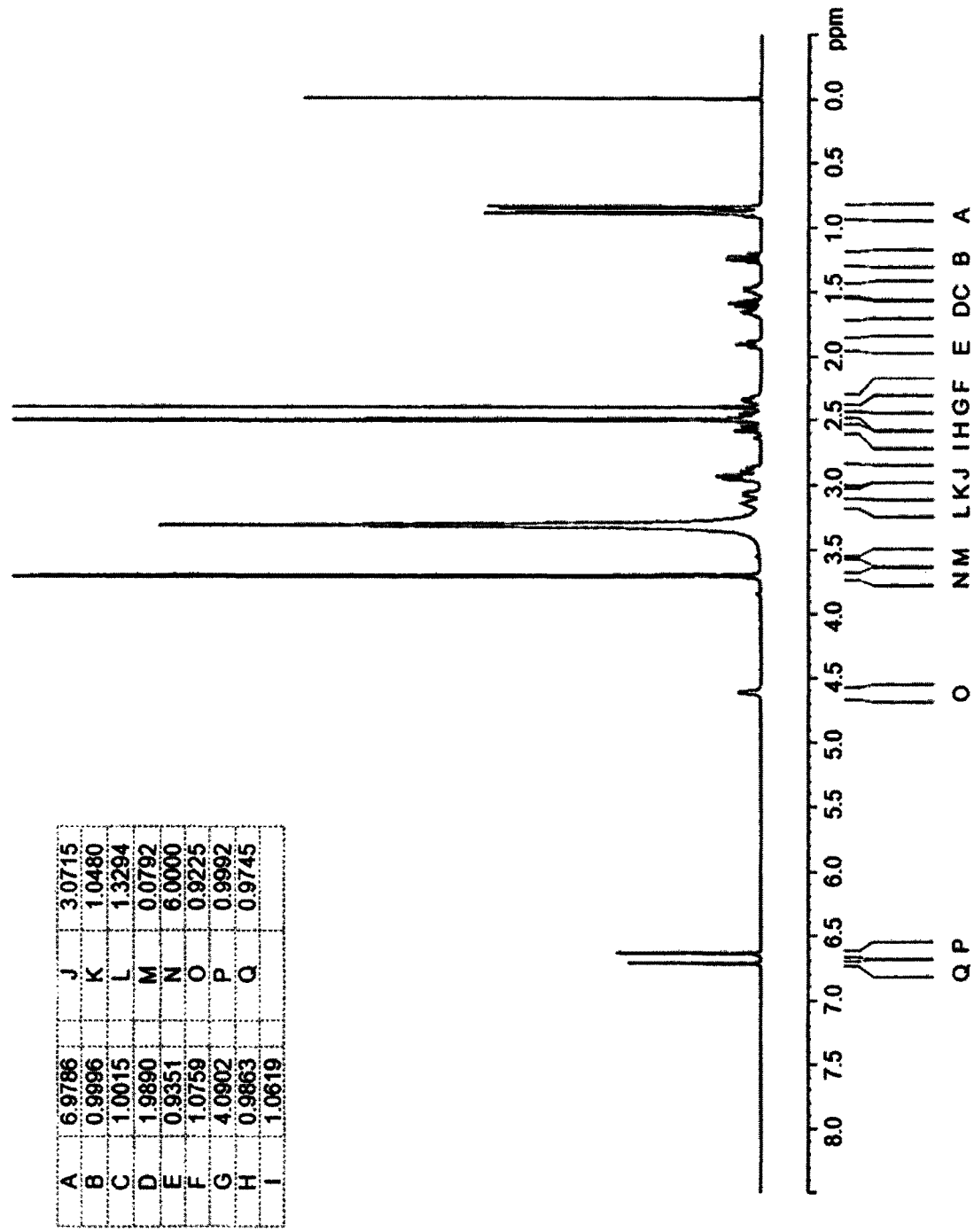
FIG. 2 shows the $^1$H NMR spectrum (recorded using DMSO as the solvent) for the (+)-α-dihydrotetrabenazine succinate salt.

The $^1$H NMR spectrum (recorded using DMSO as the solvent) for the salt is shown in FIG. 2. The $^1$H NMR spectrum confirms that the salt ratio is 1.0:1; i.e. the salt contains one mole of the free base for each mole of succinic acid.

Figure 3:
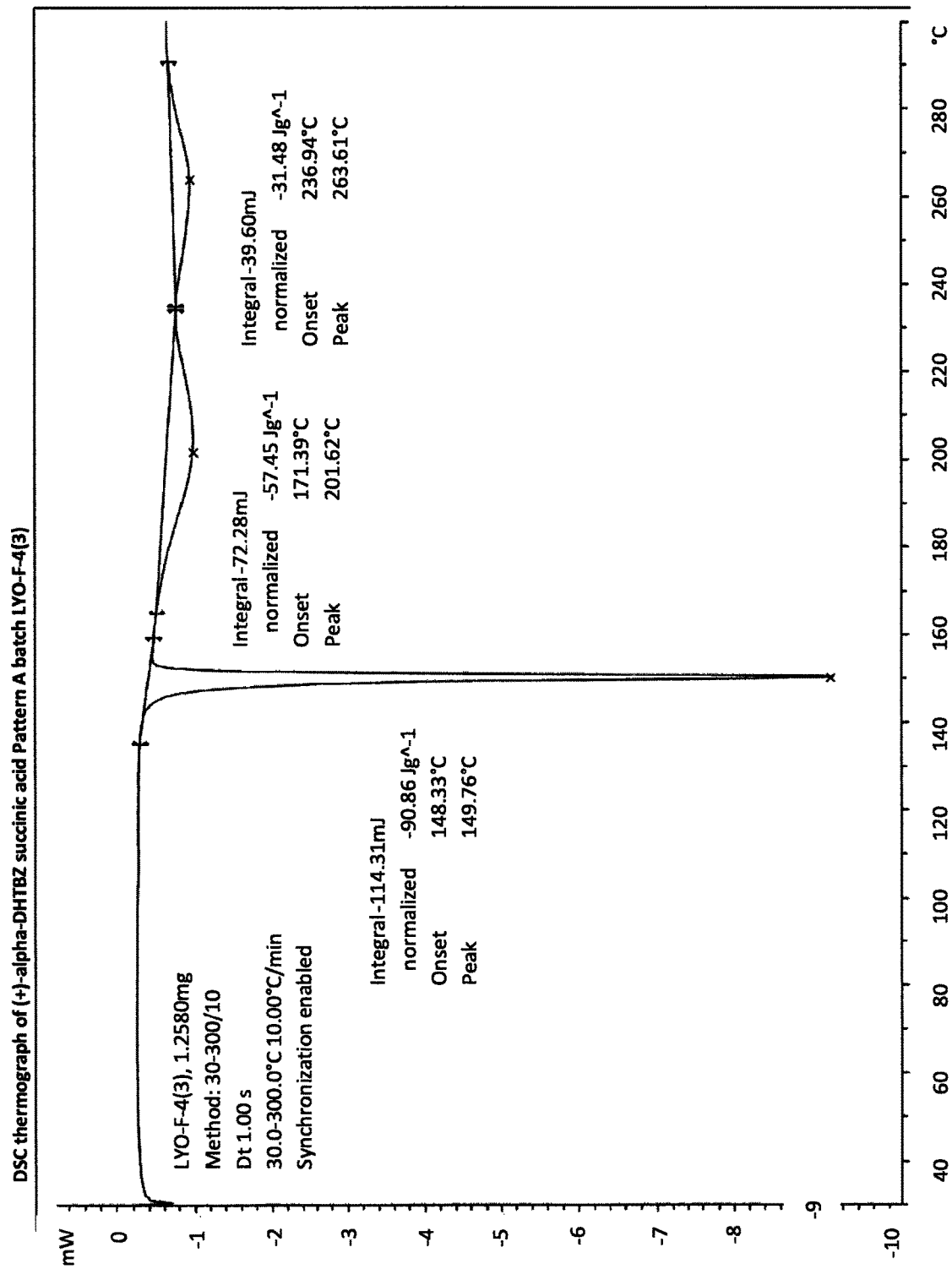
FIG. 3 shows a DSC thermogram for the (+)-α-dihydrotetrabenazine succinate salt.

The DSC thermogram for the salt is shown in FIG. 3. The thermogram shows endotherms at 150° C., 202° C. and 264° C.

Figure 4:
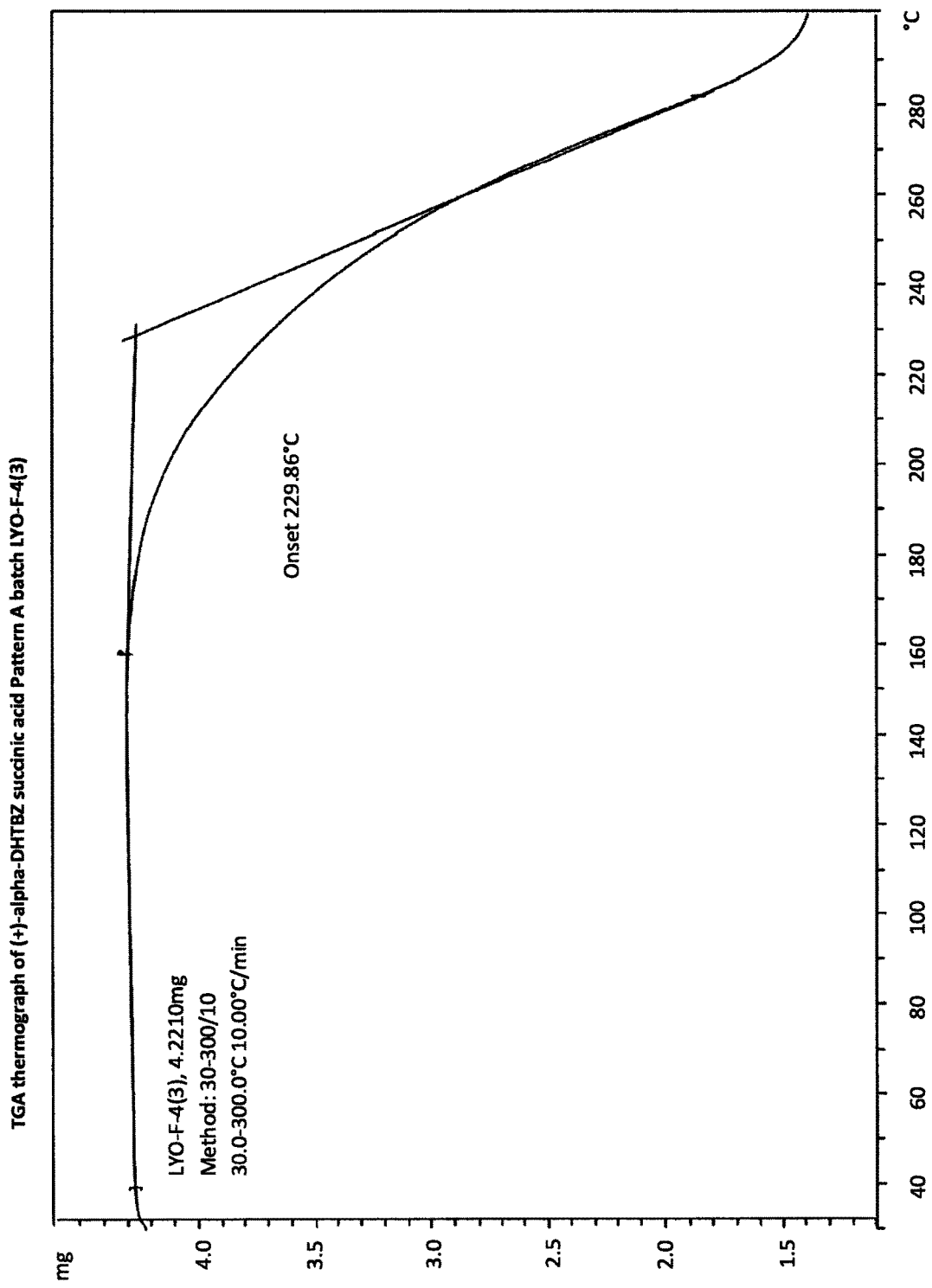
FIG. 4 shows a TGA thermogram for the (+)-α-dihydrotetrabenazine succinate salt.

The TGA thermogram for the salt is shown in FIG. 4. No weight loss was observed below 150° C.

Figure 5:
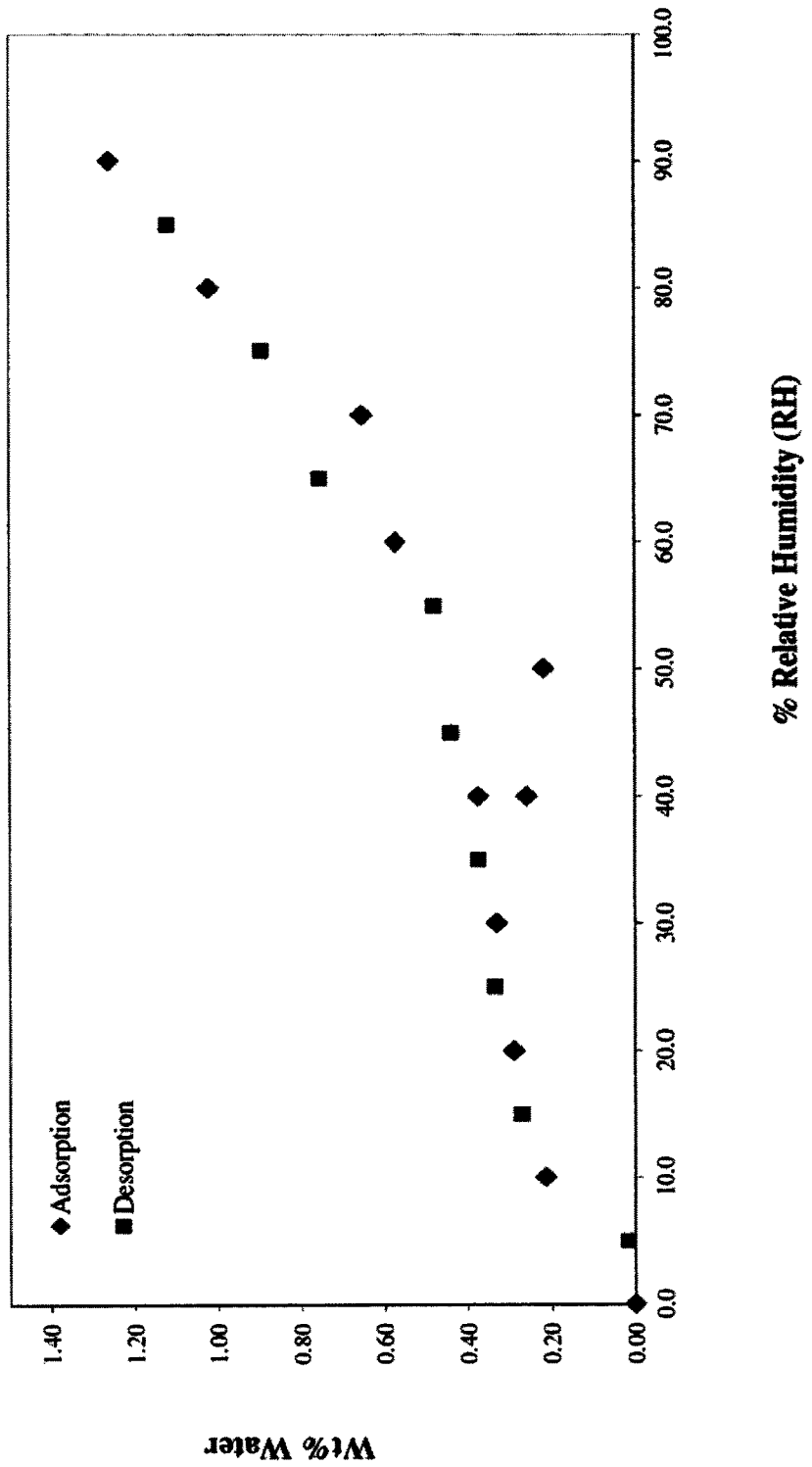
FIG. 5 is a moisture-sorption plot for the (+)-α-dihydrotetrabenazine succinate salt.
Figure 6:
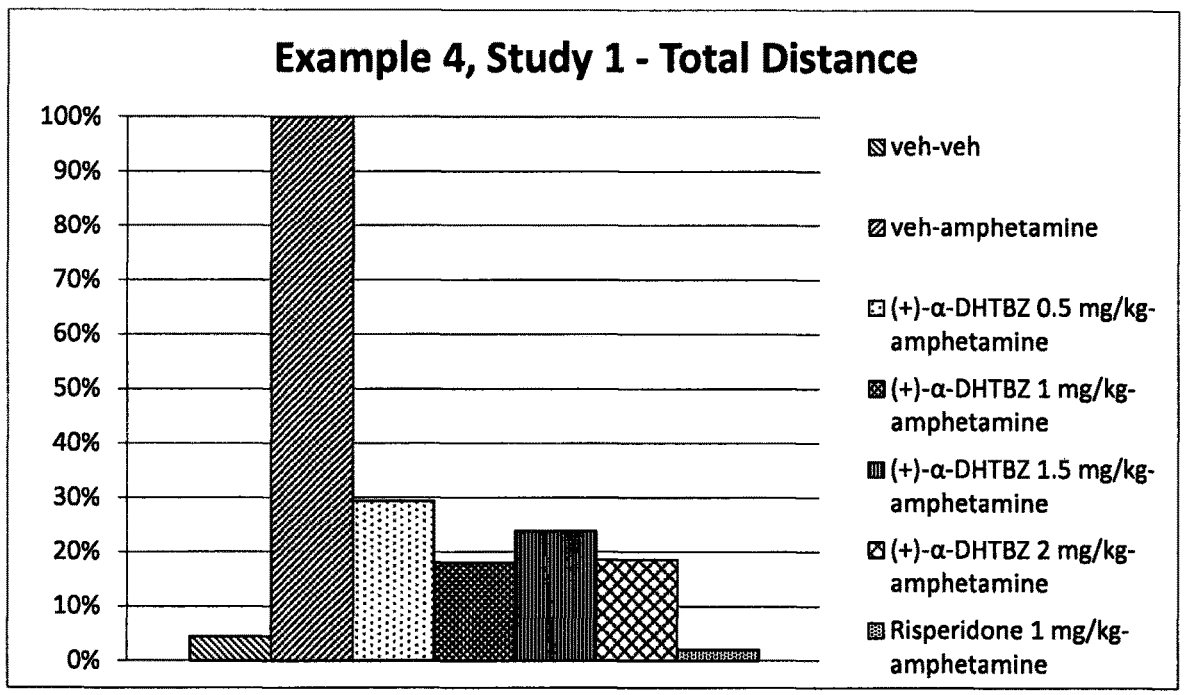
FIG. 6 shows the average total distance travelled by rats when treated with vehicle (with or without amphetamine induction) and (+)-α-dihydrotetrabenazine at doses of 0.5, 1, 1.5 and 2 mg/kg and risperidone at a dose of 1 mg/kg in amphetamine-induced rats, as described in Example 4, Study 1 below.
Figure 7:
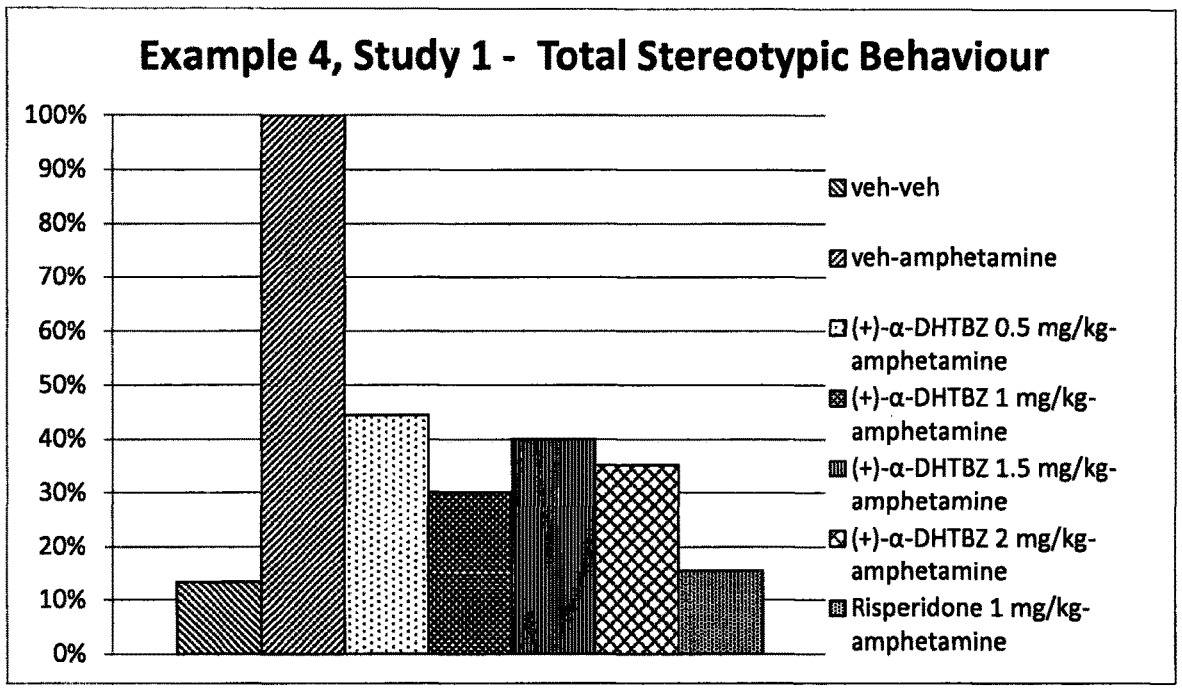
FIG. 7 shows the average total stereotypic behaviour by rats when treated with vehicle (with or without amphetamine induction) and (+)-α-dihydrotetrabenazine at doses of 0.5, 1, 1.5 and 2 mg/kg and risperidone at a dose of 1 mg/kg in amphetamine-induced rats, as described in Example 4, Study 1 below.
Figure 8:
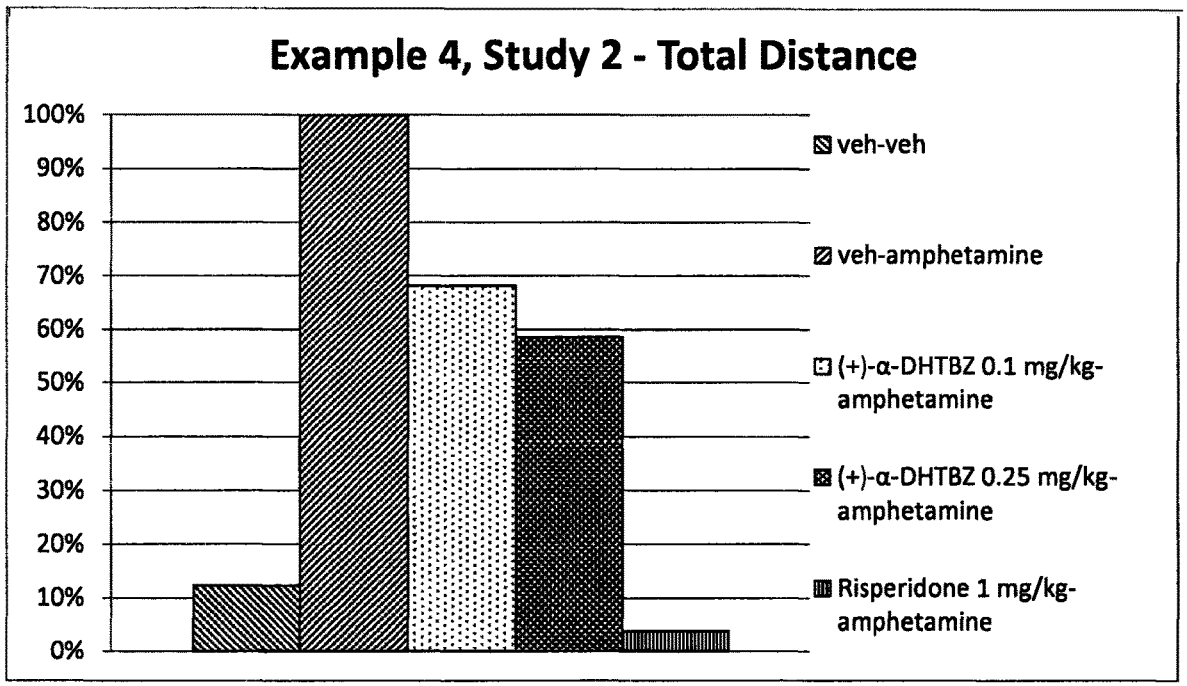
FIG. 8 shows the average total distance travelled by rats when treated with vehicle (with or without amphetamine induction) and (+)-α-dihydrotetrabenazine at doses of 0.1 mg/kg and 0.25 mg/kg and risperidone at a dose of 1 mg/kg in amphetamine-induced rats, as described in Example 4, Study 2 below.
Figure 9:
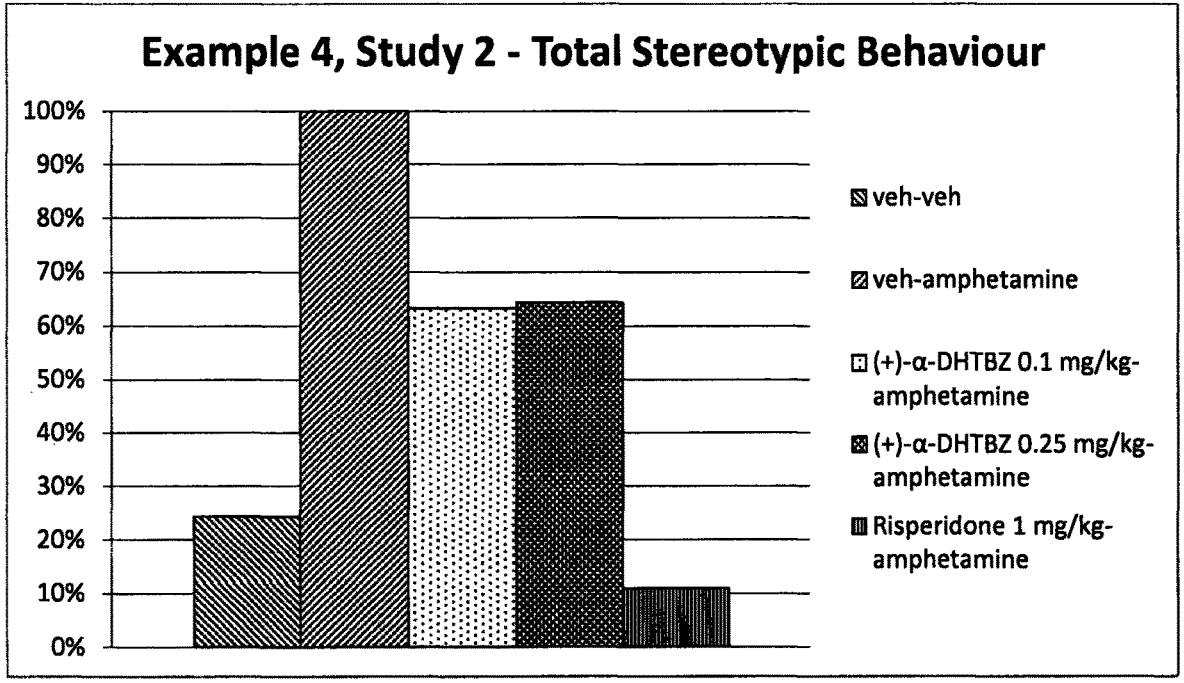
FIG. 9 shows the average total stereotypic behaviour by rats when treated with vehicle (with or without amphetamine induction) and (+)-α-dihydrotetrabenazine at doses of 0.1 mg/kg and 0.25 mg/kg and risperidone at a dose of 1 mg/kg in amphetamine-induced rats, as described in Example 4, Study 2 below.
Figure 10:
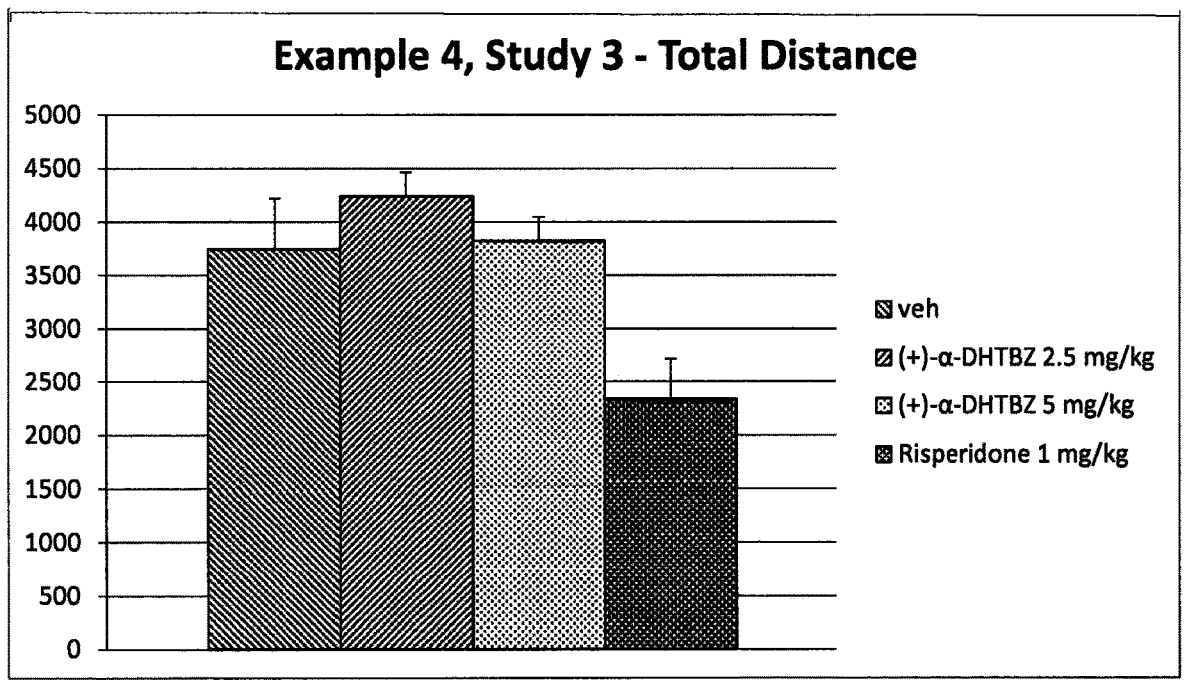
FIG. 10 shows the average total distance travelled by rats when treated with vehicle and (+)-α-dihydrotetrabenazine at a dose of 2.5 mg/kg or 5 mg/kg and risperidone at a dose of 1 mg/kg in rats without amphetamine induction, as described in Example 4, Study 3 below.
Figure 11:
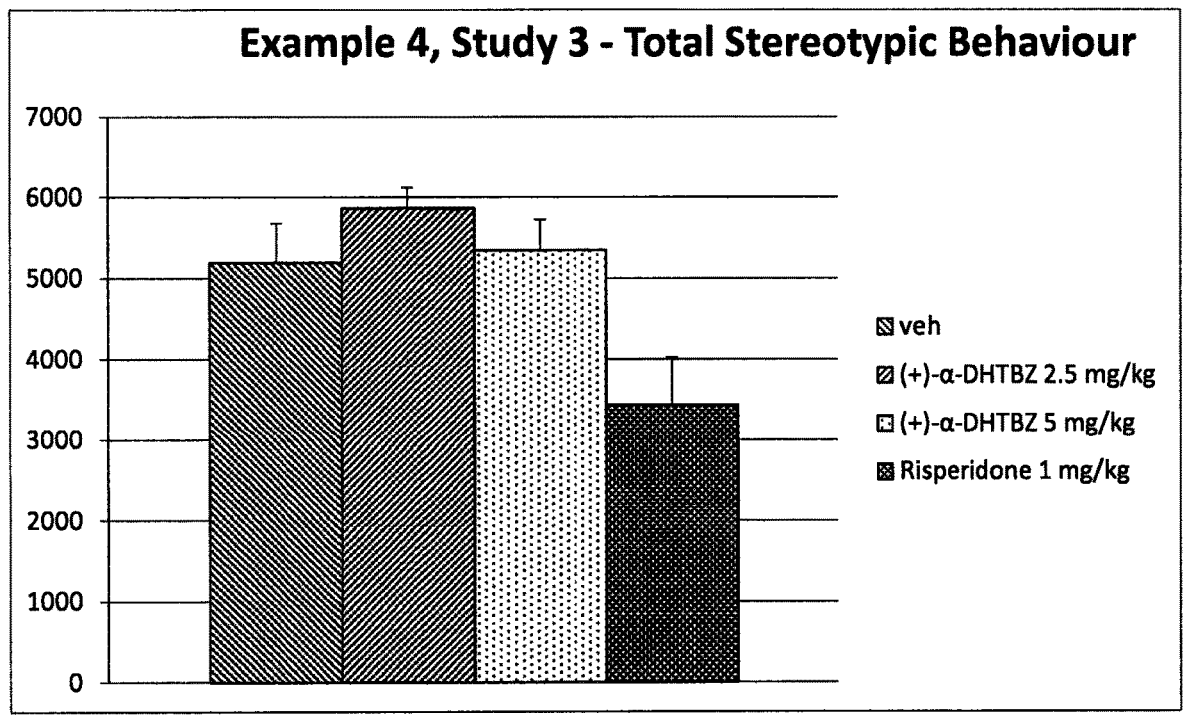
FIG. 11 shows the average total stereotypic behaviour by rats when treated with vehicle and (+)-α-dihydrotetrabenazine at a dose of 2.5 mg/kg or 5 mg/kg and risperidone at a dose of 1 mg/kg in rats without amphetamine induction, as described in Example 4, Study 3 below.

Moisture-sorption analysis was carried out and the salt was found to be slightly hygroscopic. A moisture-sorption plot is shown in FIG. 5. A moisture uptake of 0.6 weight % was observed at 60% relative humidity and a moisture uptake of 1.3 weight % was observed at 90% relative humidity. After completion of the moisture sorption studies, the salt was dried at 60° C. and 0% relative humidity and the XRPD pattern taken again (see FIG. 1 SUN-A-J-163(2)). No change from the original XRPD pattern was observed.

The analytical data described above are consistent with the succinate salt being an anhydrate.

An attempt was also made to form the hemi-succinate salt of (+)-α-dihydrotetrabenazine by mixing a solution of the free base in ethyl acetate with 0.55 molar equivalents of succinic acid in 4:1 dioxane:water at 50° C., cooling the mixture at a rate of 20° C. per hour to room temperature and then stirring overnight. The resulting solution was evaporated to form an oil. Ethyl acetate was then added to the oil and the mixture was stirred for four days at room temperature. The resulting slurry was filtered by centrifuge filtration and the isolated solids dried at room temperature overnight under reduced pressure. The dried solid was analysed by $^1$H NMR and XRPD and was identified as the mono-salt rather than the hemi-salt. The XRPD pattern is shown in FIG. 1 (see plot LYO-F-4(3)).

(+)-α-Dihydrotetrabenazine Salt Formation—Conclusions

The experiments described above demonstrate that the preparation of salts of (+)-α-dihydrotetrabenazine is not straightforward. Indeed, many acids that are known to form stable acid addition salts with other pharmacologically active compounds fail to form crystalline salts with (+)-α-dihydrotetrabenazine, or do so only with difficulty.

Of those crystalline salts that were prepared, the most water-soluble salt was the succinate salt which had a solubility (as measured by HPLC) in water of greater than 350 mg/ml. The succinate salt also had good thermal stability and no evidence of polymorphism was found. The succinate salt was the mono-salt (i.e. there is a 1:1 ratio of freebase: acid). An attempt to make the hemi-salt by using 0.55 molar equivalents of the acid failed and resulted in formation of the mono-salt. The hydrochloride salt also had good aqueous solubility (203 mg/ml) but exhibited undesirable polymorphism, with the more stable "A" crystalline form transforming to the less thermally stable "B" crystalline form when left in a aqueous slurry.

The sulphate salt suffered from variability in the salt ratio and, in none of the studies carried out, was a salt ratio characteristic of either a 1:1 salt or a hemi-salt obtained.

Finally, the benzenesulphonate salt, whilst showing good thermal stability and no apparent polymorphism, had undesirably low solubility (2.20 mg/ml compared to 0.127 mg/ml for the free base).

The most promising salt, from both a stability and solubility perspective, was therefore the succinate salt. This salt could be formed in good yield simply by stirring a slurry of the free base and the acid in acetone for a prolonged period.

Biological Properties

In the following Examples 3, 4 and 5, the biological properties of (+)-α-dihydrotetrabenazine and (+)-α-dihydrotetrabenazine succinate salt are described.

Example 3

(+)-α-Dihydrotetrabenazine in amounts was administered by oral dosing to five human volunteers. In four of the volunteers, blood sample were taken at 30, 60, 120 and 180 minutes after drug administration. Blood samples were not taken from the fifth volunteer. At 60 minutes after drug administration, PET scans were initiated and these were stopped at 120 minutes after drug administration.

The experiment was carried out at dosages of 7.5 mg, 15 mg and 22.5 mg.

Results

Table 1 shows the plasma concentrations in nanogrammes/ml of (+)-α-dihydrotetrabenazine in 4 human subjects, 0.5, 1, 1.5, 2 and 3 hours after a dose of 7.5 mg, 15 mg and 22.5 mg. Table 2 shows the % VMAT2 blocking following administration of 7.5 mg, 15 mg and 22.5 mg of (+)-α-dihydrotetrabenazine in all five subjects.

TABLE 1

| | | Subject # | | | | |
|---|---|---|---|---|---|---|
| | | 1 | 2 | 3 | 4 | 5 |
| | | Body Weight (kg) | | | | |
| Dose (oral) | Time (h) | 112 | 76 | 129 | 59 | 91 |
| 7.5 mg | 0.5 | BLQ | 0.531 | 0.216 | 8.43 | ND |
| | 1 | 0.94 | 13.7 | 4.35 | 15.0 | ND |
| | 1.5 | 2.39 | 10.8 | 6.91 | 20.7 | ND |
| | 2 | 2.44 | 14.0 | 5.03 | 17.6 | ND |
| | 3 | 3.01 | 22.2 | 6.96 | 19.6 | ND |
| 15 mg | 0.5 | 4.02 | 7.99 | 1.2 | 26.7 | ND |
| | 1 | 11.1 | 22.8 | 14.3 | 53.8 | ND |
| | 1.5 | 10.7 | 46.4 | 17.9 | 42.5 | ND |
| | 2 | 10.2 | 35.7 | 12.0 | 53.3 | ND |
| | 3 | 10.6 | 46.5 | 18.2 | 60.2 | ND |
| 22.5 mg | 0.5 | 9.61 | 5.23 | 9.04 | ND | ND |
| | 1 | 18.0 | 21.8 | 34.7 | ND | ND |
| | 1.5 | 16.8 | 36.2 | 29.8 | ND | ND |
| | 2 | 14.9 | 40.2 | 26.3 | ND | ND |
| | 3 | 13.2 | 51.8 | 17.3 | ND | ND |

BLQ—Below level of quantitation,
ND—Not done

TABLE 2

| | Subject # | | | | |
|---|---|---|---|---|---|
| | 1 | 2 | 3 | 4 | 5 |
| | Body Weight (kg) | | | | |
| Dose (oral) | 112 | 76 | 129 | 59 | 91 |
| 7.5 mg | 54 | 73 | 62 | 84 | 73 |
| 15 mg | 73 | 83 | 69 | 89 | 79 |
| 22.5 mg | 75 | 82 | 74 | ND | 82 |

Although in subjects with a lower body weight, higher (+)-α-dihydrotetrabenazine blood plasma concentrations were observed for a given dose, it can be seen that even in heavier individuals, at least 50% % VMAT2 blocking was observed at doses as low as 7.5 mg and, in lighter individuals, significantly higher % VMAT2 binding was. It was also observed that during the period of PET scanning, average plasma levels of less than 15 ng/ml gave rise to % VMAT2 binding of at least 50%. The data demonstrate that very low doses of (+)-α-dihydrotetrabenazine resulting in plasma concentrations of less than 15 ng/ml can still give high levels of VMAT2 blocking.

Example 4—Comparison of the Effect of Dihydrotetrabenazines and Risperidone on Amphetamine-Induced Hyperlocomotion Dopaminergic models for Tourette's syndrome use systemic or focal administration of dopamine agonists such as amphetamine. After injection with amphetamine, a test animal expresses stereotypic behaviour. In particular, involvement of a dopaminergic system implicated in Tourette's syndrome wild type mice and rats can be stimulated with amphetamine and the resulting hyperactivity and stereotypies can be reversed with dopamine antagonists such as risperidone and haloperidol (Tourette's syndrome—Animal Models for Screening, Charles River Discovery Research Services, Finland).

Amphetamine produced a rise in extracellular concentrations of brain dopamine and concomitant behavioural manifestations in the rat and other species. At relatively low doses (1.2 ng/kg i.p.) amphetamine increases locomotor behaviour, ceases movement and gives way to a stationary posture accompanied by highly repetitive rapid head movements. This latter non-locomotor phase of stimulation is referred to as focused stereotypy. The stereotypy can last for over an hour and is usually followed by a period of locomotor stimulation (Schiorring 1971).

Administration of dopamine agonists (such as amphetamine) is known to induce behavioural stereotypies and sensorimotor gating disruption. Also, dopaminergic, cholinergic (TANs) and HDC models (subsequent to stress and/or amphetamine injection) are known to show an increase in stereotypic behaviours (Yaol et al 2016).

Amphetamine induced stereotype behaviour has also been evaluated as a model for the movement disorder condition, tardive dyskinesia (see Rubovitis et al (1972)).

The atypical antipsychotic drug risperidone is commonly used for the treatment of Tourette's syndrome and has been described (J. D. Walkup, A Guide to Tourette Syndrome Medications, Publ. 2008, The National Tourette Syndrome Association, Inc.) as being probably the best atypical antipsychotic for tic suppression with potentially less risk of motor side effects than haloperidol and fluphenazine.

Three studies were carried out to compare the effects of dihydrotetrabenazines and risperidone on amphetamine-induced and non-amphetamine-induced hyperlocomotion in rats, on the basis that, for the reasons given above, locomotor studies are useful models for Tourette's syndrome and other movement disorders.

Materials and Methods
Equipment
  Open field arena, Med Associates Inc.
  Plastic syringes 1 ml, Terumo. Ref: SS-01T1
  Animal feeding needle 15 G, Instech Solomon, Cat: 72-4446
  Sartorius Mechatronics Scale A22101, Sartorius Weighting Technology, Germany
  Needle 27 G Terumo Myjector, 0.5 ml, Ref: 8300010463
  Plastic syringes 3 ml, Soft-Ject, Ref: 8300005761
  BD Microtainer K2EDTA tubes Ref: 365975
  Matrix 0.75 ml, Alphanum Tubes, Thermo Scientific, Ref: 4274
  Microplate Devices, Uniplate 24 wells, 10 ml, Ref: 734-1217
  Thermo Electron Corp. Heraeus Fresco 17, refrigerated centrifuge Test Animals
All animal experiments were carried out according to the National Institute of Health (NIH) guidelines for the care and use of laboratory animals, and approved by the National Animal Experiment Board, Finland. Male CD (Charles River Laboratories, Germany) at weight range of 200-250 g (165-200 g upon arrival) were used for the experiments. Animals were housed at a standard temperature (22±1° C.) and in a light-controlled environment (lights on from 7 am to 8 pm) with ad libitum access to food and water.

Methods
Locomotor activity of the rats was tested in open field arena. The open field test was performed during the rat light cycle and under a normal lighting evenly distributed to the test chambers. The paths of the rats were recorded by activity monitor (Med. Associates Inc.).

Dosing the vehicle, vehicle-amphetamine, (+)-α-DHTBZ or risperidone was done prior to LMA test. The rats were placed in the centre of the arena, and the path was recorded for 60 minutes.

Endpoint, Blood Samples and Tissue Processing
Within 10 minutes from the end of the test animals were euthanized by an overdose of $CO_2$. The terminal blood sample was collected with cardiac puncture from all compound treated rats from each group excluding vehicle rats. 0.5 ml of blood was collected with syringe attached to 18 G needle and moved into precooled K2-EDTA microtubes. The EDTA microtube was inverted several times to mix up the EDTA and blood. Tubes were then immediately put on wet ice and centrifuged (Heraeus Fresco 17) within 10-15 minutes of collecting (9.6×1000 G/10×1000 RPM, +4° C. for 2 min), and 200 μl of plasma was collected in 96-tube plates (Matrix Technologies ScreenMates 0.75 ml Alphanumeric Round-Bottom Storage tubes, PP) on dry ice according to sample map.

After collection of blood the neck was dislocated at the base of the skull. Brain was collected and weighed. Brain weights were recorded and the brain was frozen on dry ice on the 24 well plate.

The plasma and brain samples were stored at −80° C. until sent for analysis or destroyed.

Study 1
The effects on stereotypic behaviour and the distance travelled in rats following administration of (+)-α-dihydrotetrabenazine dosed at 0.5 mg/kg to 2 mg/kg, as well as risperidone at 1 mg/kg, were studied.

Animals were grouped as follows:
  Group 1: 10 rats treated with Vehicle (t=0 min) and Vehicle (t=30 min)
  Group 2: 10 rats treated with Vehicle (t=0 min) and Amphetamine (t=30 min)
  Group 3: 10 rats treated with (+)-α-DHTBZ 0.5 mg/kg (t=0 min) and Amphetamine (t=30 min)
  Group 4: 10 rats treated with (+)-α-DHTBZ 1 mg/kg (t=0 min) and Amphetamine (t=30 min)
  Group 5: 10 rats treated with (+)-α-DHTBZ 1.5 mg/kg (t=0 min) and Amphetamine (t=30 min)
  Group 6: 10 rats treated with (+)-α-DHTBZ 2 mg/kg (t=0 min) and Amphetamine (t=30 min)
  Group 7: 10 rats treated with risperidone 1 mg/kg (t=0 min) and Amphetamine (t=30 min)

Results
1. Distance Travelled
Rats dosed with either vehicle, (+)-α-DHTBZ 0.5 mg/kg, (+)-α-DHTBZ 1 mg/kg, (+)-α-DHTBZ 1.5 mg/kg, (+)-α-DHTBZ 2 mg/kg or Risperidone 1 mg/kg were subjected to LMA testing first for 30 min and then for 60 minutes after vehicle or amphetamine challenge. Resulting locomotor activity was evaluated in 3 min bins and as a total over the testing period. The normalised total distance travelled over the testing time is presented in FIG. 1.

When compared to the vehicle-vehicle group the vehicle-amphetamine was significantly different. When compared to vehicle-amphetamine group the vehicle-vehicle, (+)-α-

DHTBZ 0.5 mg/kg, (+)-α-DHTBZ 1 mg/kg, (+)-α-DHTBZ 1.5 mg/kg, (+)-α-DHTBZ 2 mg/kg and risperidone 1 mg/kg were significantly different.

2. Stereotypic Behaviour

Rats dosed with either vehicle, (+)-α-DHTBZ 0.5 mg/kg, (+)-α-DHTBZ 1 mg/kg, (+)-α-DHTBZ 1.5 mg/kg, (+)-α-DHTBZ 2 mg/kg or Risperidone 1 mg/kg were subjected to LMA testing first for 30 min and then for 60 minutes after vehicle or amphetamine challenge. Resulting stereotypic activity was evaluated in 3 min bins and as a total over the testing period. The normalised total stereotypic behaviour over the testing time is presented in FIG. 2.

When compared to the vehicle-vehicle group the vehicle-amphetamine, (+)-α-DHTBZ 0.5 mg/kg and (+)-α-DHTBZ 1.5 mg/kg were significantly different. When compared to vehicle-amphetamine group the vehicle-vehicle, (+)-α-DHTBZ 0.5 mg/kg, (+)-α-DHTBZ 1 mg/kg, (+)-α-DHTBZ 1.5 mg/kg, (+)-α-DHTBZ 2 mg/kg and risperidone 1 mg/kg were significantly different.

Conclusions

This study evaluated the effect of (+)-α-DHTBZ at doses 0.5 mg/kg, 1 mg/kg, 1.5 mg/kg and 2 mg/kg and risperidone at dose 1 mg/kg on amphetamine induced locomotor activity in male CD rats.

(+)-α-DHTBZ at all the tested doses and risperidone 1 mg/kg led to lower locomotor activity when compared to the vehicle-amphetamine group. (+)-α-DHTBZ at all the tested doses and risperidone 1 mg/kg led to reduced stereotypic behaviour when compared to the vehicle-amphetamine group. Both of the measured parameters suggest that (+)-α-DHTBZ has a sedative effect similar to risperidone.

Study 2

The effects on stereotypic behaviour and the distance travelled in rats following administration of (+)-α-dihydrotetrabenazine dosed at 0.1 mg/kg to 0.25 mg/kg, as well as risperidone at 1 mg/kg, were studied.

Animals were grouped as follows:
Group 1: 10 rats treated with Vehicle (t=0 min) and Vehicle (t=30 min)
Group 2: 10 rats treated with Vehicle (t=0 min) and Amphetamine (t=30 min)
Group 3: 10 rats treated with (+)-α-DHTBZ 0.1 mg/kg (t=0 min) and Amphetamine (t=30 min)
Group 4: 10 rats treated with (+)-α-DHTBZ 0.25 mg/kg (t=0 min) and Amphetamine (t=30 min)
Group 5: 10 rats treated with risperidone 1 mg/kg (t=0 min) and Amphetamine (t=30 min)

Results

1 Distance Travelled

Rats dosed with either vehicle, (+)-α-DHTBZ 0.1 mg/kg, (+)-α-DHTBZ 0.25 mg/kg, or Risperidone 1 mg/kg were subjected to LMA testing first for 30 min and then for 60 minutes after vehicle or amphetamine challenge. Resulting locomotor activity was evaluated in 3 min bins and as a total over the testing period. The normalised total distance travelled over the testing time is presented in FIG. 3.

When compared to vehicle-amphetamine group the vehicle-vehicle, (+)-α-DHTBZ 0.25 mg/kg and risperidone 1 mg/kg were significantly different.

2 Stereotypic Behaviour

Rats dosed with either vehicle, (+)-α-DHTBZ 0.1 mg/kg, (+)-α-DHTBZ 0.25 mg/kg, or Risperidone 1 mg/kg were subjected to LMA testing first for 30 min and then for 60 minutes after vehicle or amphetamine challenge. Resulting stereotypic activity was evaluated in 3 min bins and as a total over the testing period. The normalised total stereotypic behaviour over the testing time is presented in FIG. 4.

When compared to vehicle-amphetamine group the vehicle-vehicle, (+)-α-DHTBZ 0.1 mg/kg, (+)-α-DHTBZ 0.25 mg/kg and risperidone 1 mg/kg were significantly different.

Conclusions

This study evaluated the effect of (+)-α-DHTBZ at doses of 0.1 mg/kg and 0.25 mg/kg and risperidone at dose 1 mg/kg on amphetamine induced locomotor activity in male CD rats.

(+)-α-DHTBZ at 0.25 mg/kg and risperidone 1 mg/kg led to lower locomotor activity when compared to the vehicle-amphetamine group. (+)-α-DHTBZ at both the tested doses and risperidone 1 mg/kg led to reduced stereotypic behaviour when compared to the vehicle-amphetamine group.

Study 3

The effects of (+)-α-dihydrotetrabenazine and risperidone on in non-amphetamine induced rats was studied. Animals were grouped as follows:
Group 1: 10 rats treated with Vehicle
Group 2: 10 rats treated with (+)-α-DHTBZ 2.5 mg/kg
Group 3: 10 rats treated with (+)-α-DHTBZ 5 mg/kg
Group 4: 10 rats treated with risperidone 1 mg/kg Results In non-induced rats, the total movement and stereotypic behaviour in rats treated with the vehicle were comparable to (+)-α-dihydrotetrabenazine. However, rats treated with risperidone had reduced total movement and reduced total stereotypic behaviour.

Comments

Studies 1 and 2 in Example 4 show the effectiveness of doses of (+)-α-dihydrotetrabenazine as low as 0.1 mg/kg in reducing movement in amphetamine-induced rats. It is therefore expected that such low dose regimes may also be useful in treating hyperkinetic movement disorders in humans.

Study 3 in Example 4 suggests that following administration of low doses of (+)-α-dihydrotetrabenazine whereas abnormal movements of the type found in movement disorders will be reduced or suppressed by the drug, normal movements will not be. This is in contrast to risperidone, a well-used treatment for movement disorders, where the levels of both normal and abnormal movements can be reduced by administration of the drug.

Example 5

The objectives of this study were to provide plasma samples in order to determine the pharmacokinetic parameters of (+)-α-dihydrotetrabenazine following oral administration of (+)-α-dihydrotetrabenazine and its succinate salt to 3 male non-naive Beagle dogs (strain HsdRcc:DOBE), at a dose level of 1.50 mg/kg.

Each dog weighed approximately 9.0 to 12.0 kg and was approximately 16 to 18 months of age on the first day of dosing. Each dog was uniquely identified by indelible tattoo number.

The dogs were last used approximately 1 to 6 months prior to dosing this study. Dogs were purpose-bred, socialised and vaccinated for conventional multidisciplinary biomedical research at Envigo UK Limited, Hillcrest Research Station, Belton, Loughborough.

Prior to commencement of each dosing session, each dog was examined by a qualified Veterinary Surgeon for suitability for the study. Copies of the health and weight records of each animal were retained in the study file. Dogs were allocated to the study 5 days prior to dosing and were acclimatised in the study unit.

During the acclimatisation and study periods, the dogs were housed in pairs in purpose designed pens constructed of galvanised steel with smooth concrete floors lined with wood shavings (certificates of analysis retained in study file). The pen area was maintained at a target temperature range of 14-26° C. and was exposed to 12 hours fluorescent lighting (08:00-20:00) followed by 12 hours dark per day.

Environmental readings (temperature and humidity) were recorded daily throughout the acclimatisation and experimental period.

Administration of (+)-α-Dihydrotetrabenazine Succinate Salt

The day prior to dosing, 93.7 mg of (+)-α-dihydrotetrabenazine succinate salt (68.9 mg (+)-α-dihydrotetrabenazine freebase equivalent) was accurately weighed and then placed into a suitably sized container. On the morning of dosing, 91.87 mL of methyl cellulose solution (0.5% aq. w/v) was added to the (+)-α-dihydrotetrabenazine succinate salt and then sonicated for ca. 5 minutes at ambient temperature, prior to being stirred at room temperature for ca. 15 minutes. The final dose yielded a clear solution containing (+)-α-dihydrotetrabenazine succinate salt at target concentration of 0.75 mg/mL dihydrotetrabenazine freebase equivalent.

Doses were administered orally, via gavage, at a dose volume of 2.00 mL/kg yielding the target dose level of 1.50 mg/kg. Following dosing, 10 mL of tap water was flushed down the gavage to ensure the entire dose was dispensed.

Following dosing over four sessions each with one of the test materials, serial whole blood samples (circa. 1.3 mL) were collected from a jugular vein then placed into $K_2$ EDTA treated tubes pre-dose and then 0.25, 0.50, 1, 2, 3, 4, 6, 12 and 24 hours post dose.

Blood samples were placed immediately on a cool-block before being centrifuged within 15 minutes at 3,000×g, 10 minutes, 4° C. and resultant plasma drawn off.

Administration of (+)-α-Dihydrotetrabenazine

The day prior to dosing, 72.9 mg of (+)-α-dihydrotetrabenazine was accurately weighed then placed into a suitably sized container. On the morning of dosing, 97.23 mL of methyl cellulose solution (0.5% aq. w/v) was added to the test material then sonicated for ca. 5 minutes at ambient temperature, prior to being stirred at room temperature for ca. 10 minutes. The final dose yielded a very fine homogenous suspension containing (+)-α-dihydrotetrabenazine at target concentration of 0.75 mg/mL which was constantly stirred throughout the dosing period.

Doses were administered orally, via gavage, at a dose volume of 2.00 mL/kg yielding the target dose level of 1.50 mg/kg. Following dosing, 10 mL of tap water was flushed down the gavage to ensure the entire dose was dispensed.

Following dosing over four sessions each with one of the test materials, serial whole blood samples (circa. 1.3 mL) were collected from a jugular vein then placed into $K_2$ EDTA treated tubes pre-dose and then 0.25, 0.50, 1, 2, 3, 4, 6, 12 and 24 hours post dose.

Blood samples were placed immediately on a cool-block before being centrifuged within 15 minutes at 3,000×g, 10 minutes, 4° C. and resultant plasma drawn off.

Results

The (+)-α-dihydrotetrabenazine plasma concentrations are shown in Tables 3 and 4 below.

Table 3 shows the plasma concentrations of (+)-α-dihydrotetrabenazine in the male Beagle dogs following oral administration of (+)α-dihydrotetrabenazine succinate salt at a dose level of 1.50 mg/kg (dihydro tetrabenazine freebase equivalent).

TABLE 3

| Time Point | Plasma concentration (ng/mL) | | | | |
|---|---|---|---|---|---|
| (Hrs.) | Male 1 | Male 2 | Male 3 | Mean | SD |
| 0 | BLQ | BLQ | BLQ | 0.00 | 0.00 |
| 0.25 | 66.7 | 43.2 | 28.0 | 45.97 | 19.50 |
| 0.5 | 47.6 | 32.4 | 83.1 | 54.37 | 26.02 |
| 1 | 23.4 | 14.8 | 49.2 | 29.13 | 17.90 |
| 2 | 7.04 | 3.65 | 21.7 | 10.80 | 9.59 |
| 3 | 2.48 | 1.23 | 10.6 | 4.77 | 5.09 |
| 4 | 1.03 | 0.531 | 6.21 | 2.59 | 3.14 |
| 6 | 0.304 | BLQ | 1.68 | 0.66 | 0.90 |
| 12 | BLQ | BLQ | 0.212 | 0.07 | 0.12 |
| 24 | BLQ | BLQ | BLQ | 0.00 | 0.00 |

BLQ—Below the limit of quantitation (<0.10 ng/mL)
BLQ values are treated as zero for the purposes of calculating the mean and SD values Table 4 shows the plasma concentrations of (+)-α-dihydrotetrabenazine in the male Beagle dog following oral administration of (+)-α-dihydrotetrabenazine at a dose level of 1.50 mg/kg

TABLE 4

| Time Point | Plasma concentration (ng/mL) | | | | |
|---|---|---|---|---|---|
| (Hrs.) | Male 1 | Male 2 | Male 3 | Mean | SD |
| 0 | BLQ | BLQ | BLQ | 0.00 | 0.00 |
| 0.25 | 48.9 | 20.2 | 107 | 58.70 | 44.22 |
| 0.5 | 39.2 | 18.3 | 65.0 | 40.83 | 23.39 |
| 1 | 24.2 | 9.63 | 40.5 | 24.78 | 15.44 |
| 2 | 7.21 | 2.72 | 17.2 | 9.04 | 7.41 |
| 3 | 2.51 | 0.798 | 9.72 | 4.34 | 4.73 |
| 4 | 1.04 | 0.359 | 4.73 | 2.04 | 2.35 |
| 6 | 0.367 | 0.113 | 1.42 | 0.63 | 0.69 |
| 12 | BLQ | BLQ | 0.168 | 0.06 | 0.10 |
| 24 | BLQ | BLQ | BLQ | 0.00 | 0.00 |

BLQ—Below the limit of quantitation (<0.10 ng/mL)
BLQ values are treated as zero for the purposes of calculating the mean and SD values Following administration of (+)-α-dihydrotetrabenazine succinate salt, a mean $C_{max}$ blood plasma concentration of (+)-α-dihydrotetrabenazine of 64.33 ng/mL was observed on average 0.33 hours post dose with the corresponding exposure being 71.8782 ng·h·mL.

(+)-α-dihydrotetrabenazine resulted in similar results to (+)-α-dihydrotetrabenazine succinate salt with a (+)-α-dihydrotetrabenazine $C_{max}$ of 58.7 ng/mL, observed at 0.25 hour post dose, with a mean exposure being 64.26 ng·h·mL.

Comments

These studies show that (+)-α-dihydrotetrabenazine succinate salt can be converted in vivo to (+)-α-dihydrotetrabenazine and provides (+)-α-dihydrotetrabenazine blood plasma levels comparable to those obtained when (+)-α-dihydrotetrabenazine free base is administered.

EQUIVALENTS

It will readily be apparent that numerous modifications and alterations may be made to the specific embodiments of the invention described above without departing from the principles underlying the invention. All such modifications and alterations are intended to be embraced by this application.

The invention claimed is:
1. A method of treatment of a movement disorder in a subject in need thereof, which method comprises administering to the subject a therapeutically effective amount of (+)-α-dihydrotetrabenazine succinate.

2. A method according to claim 1 wherein the movement disorder is a hyperkinetic movement disorder.

3. A method according to claim 2 wherein the hyperkinetic movement disorder is selected from Huntington's disease, hemiballismus, senile chorea, tic disorders, tardive dyskinesia, dystonia and Tourette's syndrome.

4. A method according to claim 3 wherein the hyperkinetic movement disorder is Tourette's syndrome.

5. A method according to claim 1 wherein the subject is a mammalian subject.

6. A method according to claim 5 wherein the subject is a human.

7. A method according to claim 1 wherein the treatment comprises administering to the subject an amount of (+)-α-dihydrotetrabenazine succinate between 1 mg and 30 mg per day.

8. A method according to claim 7 wherein the treatment comprises administering to the subject an amount of (+)-α-dihydrotetrabenazine succinate between 2 mg and 20 mg per day.

9. A method according to claim 1 wherein the (+)-α-dihydrotetrabenazine succinate salt is in a crystalline form.

10. A method according to claim 1 wherein the (+)-α-dihydrotetrabenazine succinate salt has a salt ratio of approximately 1:1.

11. A method according to claim 1 wherein the (+)-α-dihydrotetrabenazine succinate salt is in a substantially crystalline form having an X-ray powder diffraction pattern characterized by the presence of major peaks at the diffraction angles of approximately 9.2° and/or 10.0° and/or 18.5° and/or 22.4°.

12. A method according to claim 1 wherein the (+)-α-dihydrotetrabenazine succinate salt is in a substantially crystalline form having an X-ray powder diffraction pattern substantially as shown in any of plots ZEN-E-6-7b, LYO-F-4(3), SUN-AJ-163(2) or SUN-AJ-163(2) AD in FIG. 1.

13. A method according to claim 1 wherein the (+)-α-dihydrotetrabenazine succinate salt is in a substantially crystalline form having an X-ray powder diffraction pattern substantially as shown in plot SUN-AJ-163(2) in FIG. 1.

14. A method according to claim 10 wherein the movement disorder is a hyperkinetic movement disorder.

15. A method according to claim 14 wherein the hyperkinetic movement disorder is selected from Huntington's disease, hemiballismus, senile chorea, tic disorders, tardive dyskinesia, dystonia and Tourette's syndrome.

16. A method according to claim 15 wherein the hyperkinetic movement disorder is Tourette's syndrome.

* * * * *